US012776049B2

(12) United States Patent
Cameron et al.

(10) Patent No.: US 12,776,049 B2
(45) Date of Patent: Oct. 27, 2026

(54) PATIENT REGISTRATION FOR TOTAL HIP ARTHROPLASTY PROCEDURE USING PRE-OPERATIVE COMPUTED TOMOGRAPHY (CT), INTRA-OPERATIVE FLUOROSCOPY, AND/OR POINT CLOUD DATA

(71) Applicant: GLOBUS MEDICAL, INC., Audubon, PA (US)

(72) Inventors: Hayden Cameron, Philadelphia, PA (US); Richard H. Washburn, II, Wayne, PA (US); Israel Oluwasakin, Dresher, PA (US); Stephen Cragg, Philadelphia, PA (US); Loris Duch, Bretigny-sur-Morrens (CH); Benoit Brot, Lausanne (CH)

(73) Assignee: Globus Medical, Inc., Audubon, PA (US)

( * ) Notice: Subject to any disclaimer, the term of this patent is extended or adjusted under 35 U.S.C. 154(b) by 175 days.

(21) Appl. No.: 18/743,388

(22) Filed: Jun. 14, 2024

(65) Prior Publication Data

US 2025/0384568 A1 Dec. 18, 2025

(51) Int. Cl.

| | |
|---|---|
| ***G06T 7/33*** | (2017.01) |
| ***A61B 6/00*** | (2024.01) |
| ***A61B 6/50*** | (2024.01) |
| ***A61B 34/10*** | (2016.01) |
| ***A61B 34/20*** | (2016.01) |
| ***G06T 7/11*** | (2017.01) |
| ***G06T 15/08*** | (2011.01) |

(52) U.S. Cl.

CPC .............. *G06T 7/344* (2017.01); *A61B 6/487* (2013.01); *A61B 6/505* (2013.01); *A61B 6/5235* (2013.01); *A61B 34/10* (2016.02); *A61B 34/20* (2016.02); *G06T 7/11* (2017.01); *G06T 15/08* (2013.01); *A61B 2034/105* (2016.02); *A61B 2034/2065* (2016.02); *A61B 2034/207* (2016.02); *G06T 2200/24* (2013.01); *G06T 2207/10081* (2013.01); *G06T 2207/10121* (2013.01); *G06T 2207/20081* (2013.01); *G06T 2207/20084* (2013.01); *G06T 2207/30008* (2013.01); *G06T 2210/41* (2013.01)

(58) Field of Classification Search

CPC ...................................................... G06T 7/344

See application file for complete search history.

(56) References Cited

U.S. PATENT DOCUMENTS

| | | | |
|---|---|---|---|
| 7,835,784 B2 | 11/2010 | Mire et al. |
| 7,949,386 B2 | 5/2011 | Buly et al. |
| 8,078,254 B2 | 12/2011 | Murphy |
| 8,175,683 B2 | 5/2012 | Roose |
| 8,675,939 B2 | 3/2014 | Moctezuma de la Barrera |
| 8,679,125 B2 | 3/2014 | Smith et al. |

(Continued)

*Primary Examiner* — Shivang I Patel

(57) ABSTRACT

A system for computer assisted navigation during surgery includes a computer platform that operates to register a target surgical area of a patient. In certain cases, a process includes: obtaining a pre-op CT image of a pelvic region of a patient and intra-operatively obtaining a point cloud data about the pelvic region with a navigated instrument, generating a 3D bone model which excludes non-targeted area such as a femur, and then merging the 3D bone model to the point cloud to register the target surgical area.

20 Claims, 29 Drawing Sheets

(56) References Cited

U.S. PATENT DOCUMENTS

| | | | |
|---|---|---|---|
| 8,744,819 B2 | 6/2014 | Rodriguez Y Baena | |
| 8,774,900 B2 | 7/2014 | Buly et al. | |
| 8,888,782 B2 | 11/2014 | Smith et al. | |
| 9,095,375 B2 | 8/2015 | Haimerl et al. | |
| 9,248,002 B2 | 2/2016 | McCarthy | |
| 9,456,874 B2 | 10/2016 | Kubiak et al. | |
| 9,610,134 B2 | 4/2017 | Kubiak et al. | |
| 9,662,228 B2 | 5/2017 | McCarthy | |
| 9,916,422 B2 | 3/2018 | Haimerl | |
| 9,947,110 B2 | 4/2018 | Haimerl | |
| 9,949,797 B2 | 4/2018 | Meridew et al. | |
| 9,968,456 B2 | 5/2018 | Song | |
| 10,092,361 B2 | 10/2018 | Ferro et al. | |
| 10,105,168 B2 | 10/2018 | Blau | |
| 10,219,865 B2 | 3/2019 | Jansen et al. | |
| 10,231,786 B2 | 3/2019 | Ferro et al. | |
| 10,433,914 B2 | 10/2019 | Wollowick et al. | |
| 10,485,450 B2 | 11/2019 | Gupta et al. | |
| 10,500,067 B2 | 12/2019 | McCarthy | |
| 10,540,479 B2 | 1/2020 | Murphy et al. | |
| 10,765,384 B2 | 9/2020 | Wollowick et al. | |
| 10,827,998 B2 | 11/2020 | Simon et al. | |
| 10,864,047 B2 | 12/2020 | Hagag et al. | |
| 10,869,724 B2 | 12/2020 | Beck et al. | |
| 10,874,469 B2 | 12/2020 | Zheng et al. | |
| 10,918,398 B2 | 2/2021 | Fouts et al. | |
| 10,959,857 B2 | 3/2021 | Wu et al. | |
| 10,973,590 B2 | 4/2021 | Boddington et al. | |
| 11,007,013 B2 | 5/2021 | Hladio et al. | |
| 11,020,183 B2 | 6/2021 | Gomes | |
| 11,020,189 B2 | 6/2021 | Tao et al. | |
| 11,107,586 B1 | 8/2021 | DeCook et al. | |
| 11,219,486 B2 | 1/2022 | Meridew et al. | |
| 11,246,508 B2 | 2/2022 | Gupta et al. | |
| 11,257,241 B2 | 2/2022 | Tao | |
| 11,311,339 B2 | 4/2022 | Jansen et al. | |
| 11,318,025 B2 | 5/2022 | Schipper et al. | |
| 11,331,151 B2 | 5/2022 | Mahfouz | |
| 11,337,762 B2 | 5/2022 | McKinnon et al. | |
| 11,389,251 B2 | 7/2022 | Dohmen et al. | |
| 11,413,095 B2 | 8/2022 | Hladio et al. | |
| 11,426,241 B2 | 8/2022 | Jeszenszky et al. | |
| 11,478,207 B2 | 10/2022 | Simon et al. | |
| 11,523,868 B2 | 12/2022 | Tan et al. | |
| 11,622,811 B1 | 4/2023 | Song et al. | |
| 11,622,813 B2 | 4/2023 | Ferro et al. | |
| 11,642,155 B2 | 5/2023 | Blau | |
| 11,642,174 B2 | 5/2023 | Wollowick et al. | |
| 11,669,984 B2 | 6/2023 | Siewerdsen et al. | |
| 11,741,619 B2 | 8/2023 | Aghdasi et al. | |
| 11,813,052 B2 | 11/2023 | Gupta et al. | |
| 11,826,111 B2 | 11/2023 | Mahfouz | |
| 11,865,008 B2 | 1/2024 | Fanson et al. | |
| 11,883,219 B2 | 1/2024 | Boddington et al. | |
| 11,887,306 B2 | 1/2024 | Cooper et al. | |
| 11,925,502 B2 | 3/2024 | Amiri | |
| 2019/0320995 A1 | 10/2019 | Amiri | |
| 2020/0352529 A1 | 11/2020 | Wollowick et al. | |
| 2020/0405180 A1 | 12/2020 | Macht | |
| 2021/0145517 A1 | 5/2021 | Pierrepont et al. | |
| 2022/0087747 A1 | 3/2022 | Meridew et al. | |
| 2022/0192755 A1 | 6/2022 | Siccardi et al. | |
| 2022/0296193 A1 | 9/2022 | Grupp et al. | |
| 2022/0323159 A1 | 10/2022 | Boettner et al. | |
| 2022/0361955 A1 | 11/2022 | Signoretti et al. | |
| 2023/0000556 A1 | 1/2023 | McKinnon et al. | |
| 2023/0019873 A1* | 1/2023 | Landon .................. | G06T 19/20 |
| 2023/0068971 A1 | 3/2023 | Derouault et al. | |
| 2023/0105822 A1 | 4/2023 | Miles et al. | |
| 2023/0105898 A1 | 4/2023 | Miles et al. | |
| 2023/0108487 A1 | 4/2023 | Miles et al. | |
| 2023/0118746 A1 | 4/2023 | Hettich et al. | |
| 2023/0218323 A1 | 7/2023 | Blau | |
| 2023/0368465 A1 | 11/2023 | Mahfouz et al. | |
| 2023/0368922 A1 | 11/2023 | DeCook et al. | |
| 2023/0414287 A1 | 12/2023 | de Souza et al. | |
| 2024/0033007 A1 | 2/2024 | Beck et al. | |
| 2024/0261030 A1* | 8/2024 | Long ..................... | A61B 34/10 |

* cited by examiner

PATIENT REGISTRATION FOR TOTAL HIP ARTHROPLASTY PROCEDURE USING PRE-OPERATIVE COMPUTED TOMOGRAPHY (CT), INTRA-OPERATIVE FLUOROSCOPY, AND/OR POINT CLOUD DATA

FIELD

The present disclosure relates to medical devices and systems, and more particularly, surgical navigation systems for hip surgery.

BACKGROUND

Computer assisted surgery navigation systems have become a well-established technique in operating rooms for providing surgeons with computerized visualization of how a surgical instrument or other device that is posed relative to a patient correlates to a pose relative to medical images of the patient's anatomy, and how those poses correlate to a pre-operative surgical plan. Camera tracking systems for computer assisted surgery navigation typically use a set of tracking cameras to track a pose of a reference element on the surgical instrument, which is being positioned by a surgeon during surgery, relative to a patient reference element (also "dynamic reference base" (DRB)) affixed to a patient. A computer model of a real instrument is associated with a reference element, so that the computer model can be overlaid on registered images of patient's anatomy. The camera tracking system uses the relative poses of the reference elements to determine how the real instrument is posed relative to a patient and to determine how the computer model of the real instrument is to be correspondingly posed as overlaid on the medical images. The surgeon can thereby use real-time visual feedback of the relative poses to navigate the surgical instrument during a surgical procedure on the patient.

A robotic system for arthroplasty procedures can be used which has a serial arm on which a passive structure guiding the saw blade is mounted. For example, a sagittal saw can be attached to the end of the passive structure to guide the cutting plane. The system can enable a surgeon to hold the sagittal saw and cut bones while watching on the navigation system (e.g., stand-alone displays or Augmented Reality (AR) headset), and to receive various types of relevant feedback and information associated with a defined plan for and/or progress of the surgical procedure.

The serial arm can moved through computer guided control to a suitable position for the surgery, e.g., pursuant to the surgeon's request which may be provided via a foot pedal, touchscreen, AR interaction, etc. The passive structure allows the surgeon to precisely remove bone in the cutting plane. Bone removal progression can be measured through camera tracking of fiducials of a reference element attached to the bones and to the sagittal saw.

Various workflows can be available for use with the system. Some workflows require preoperative scans or images of the patient (e.g., x-ray, Computerized Tomography (CT)). On the other hand, an imageless workflow does not require any pre-operative images. To obtain intra-operative information about the patient anatomy, the surgeon measures key parameters of the bone using a camera tracking system and an appropriate tracked instrument to capture points on patient anatomy. Later, this information is used to plan the implant position and orientation with respect to patient anatomy and to navigate the robot and surgical instruments during the surgical procedure.

Some workflows include having the surgeon rigidly attach a reference element to one or more bones, where the reference element includes fiducials which are detected by tracking cameras for computer assisted navigation. The reference elements allow tracking of bone position by the navigation system. The reference elements can be positioned on the bone and oriented such that they can be seen by the tracking cameras of the navigation system. Once positioned, the reference elements are attached with fixation structures (e.g., screw pins, "crocodile" jaws) on the bone (e.g., pelvis or femur and tibia depending on surgical procedure being performed). The reference elements' respective positions and orientations stay rigidly fixed with respect to the bone throughout the procedure.

Another step of various workflows is to register the patient in the tracking space of the navigation system. Patient registration can include matching the patient anatomy with a numeric representation of the corresponding bone, such as a three-dimensional (3D) model of the bone. The bone representation may be either constructed from a set of CT images (CT workflow) or based on a generic bone model (Imageless workflow).

Particular surgical procedures can pose challenges in patient registration, for example, where anatomical features make imaging more challenging and/or where surgical access to such features is limited. One example of such a procedure is total hip arthroplasty (THA), where imaging of the pelvic operating area (or, acetabulum) often includes non-target regions such as the femur.

Although current surgical approaches offer sophisticated computer assisted navigation once bone landmarks of a patient have been properly registered for tracking, current approaches for registration can have shortcomings, e.g., in THA procedures.

SUMMARY

Various embodiments include a system for computer assisted navigation during surgery including a computer platform that operates to register a target surgical area of a patient. In certain cases, a process includes: obtaining images of a pelvic region of a patient and/or point cloud data about the pelvic region of a patient, merging the images and/or point cloud data by applying a set of merge rules to exclude a non-target surgical area, and registering a location of the target surgical area based on the merger.

Some embodiments of the present disclosure are directed to a system for computer assisted navigation during surgery. Certain systems include a computer platform that operates to obtain a computed tomography (CT) image of a pelvic region of a patient captured prior to the surgery, where the CT image of the pelvic region includes a target surgical area and a non-target surgical area. The system further obtains a fluoroscopy image of the pelvic region of the patient captured during the surgery, and merges the CT image and the fluoroscopy image by applying a set of merge rules to exclude the non-target surgical area. The system further registers register a location of the target surgical area based on the merged CT image and fluoroscopy image.

Some other corresponding embodiments of the present disclosure are directed to a computer program product comprising a non-transitory computer readable medium storing instructions executable by at least one processor to perform operations for computer assisted navigation during surgery. The operations obtain a computed tomography (CT)

image of a pelvic region of a patient captured prior to the surgery, the CT image of the pelvic region including a target surgical area and a non-target surgical area. The operations further obtain a fluoroscopy image of the pelvic region of the patient captured during the surgery, and merge the CT image and the fluoroscopy image by applying a set of merge rules to exclude the non-target surgical area. The operations further register a location of the target surgical area based on the merged CT image and fluoroscopy image.

Certain additional embodiments include a system for computer assisted navigation during a surgery, comprising a computer platform operative to: obtain a computed tomography (CT) image of a pelvic region of a patient captured prior to the surgery, where the CT image of the pelvic region includes a target surgical area and a non-target surgical area, obtain a point cloud of the pelvic region of the patient with a navigated instrument during the surgery, merge the CT image and the point cloud by applying a set of merge rules to exclude the non-target surgical area, and register a location of the target surgical area based on the merged CT image and point cloud.

Certain additional embodiments include a computer program product comprising a non-transitory computer readable medium storing instructions executable by at least one processor to perform operations for computer assisted navigation during surgery to: obtain a computed tomography (CT) image of a pelvic region of a patient captured prior to the surgery, where the CT image of the pelvic region includes a target surgical area and a non-target surgical area, obtain a point cloud of the pelvic region of the patient with a navigated instrument during the surgery, merge the CT image and the point cloud by applying a set of merge rules to exclude the non-target surgical area, and register a location of the target surgical area based on the merged CT image and point cloud.

Certain additional embodiments include a system for computer assisted navigation during a surgery, comprising a computer platform operative to: obtain a plurality of fluoroscopy images of the pelvic region of the patient captured during the surgery, where the plurality of fluoroscopy images of the pelvic region include a target surgical area and a non-target surgical area, identify a functional pelvic plane (FPP) in the plurality of fluoroscopy images, identify an anterior pelvic plane (APP) in the plurality of fluoroscopy images, merge the FPP image and APP image by applying a set of merge rules to exclude the non-target surgical area, and register a location of the target surgical area based on the merged FPP image and APP image.

Certain additional embodiments include a computer program product comprising a non-transitory computer readable medium storing instructions executable by at least one processor to perform operations for computer assisted navigation during surgery to: obtain a plurality of fluoroscopy images of the pelvic region of the patient captured during the surgery, where the plurality of fluoroscopy images of the pelvic region include a target surgical area and a non-target surgical area, identify a functional pelvic plane (FPP) in the plurality of fluoroscopy images, identify an anterior pelvic plane (APP), merge the FPP image and APP image by applying a set of merge rules to exclude the non-target surgical area, and register a location of the target surgical area based on the merged FPP image and APP image.

Certain additional embodiments include a system for computer assisted navigation during a surgery, comprising a computer platform operative to: obtain a fluoroscopy image of the pelvic region of the patient captured during the surgery, determine a first center of rotation (C1) of an acetabulum of the patient in the fluoroscopy image, determine a second center of rotation (C2) of the acetabulum of the patient using a navigated instrument trackable by an optical tracking device, and register the fluoroscopy image in an optical coordinate system of the optical tracking device based on the determined first center of rotation (C1) and second center of rotation (C2).

Certain additional embodiments include a computer program product comprising a non-transitory computer readable medium storing instructions executable by at least one processor to perform operations for computer assisted navigation during surgery to: obtain a fluoroscopy image of the pelvic region of the patient captured during the surgery, determine a first center of rotation (C1) of an acetabulum of the patient in the fluoroscopy image, determine a second center of rotation (C2) of the acetabulum of the patient using a navigated instrument trackable by an optical tracking device, and register the fluoroscopy image in an optical coordinate system of the optical tracking device based on the determined first center of rotation (C1) and second center of rotation (C2).

Other systems for computer assisted navigation during surgery, computer program products, and related methods for computer assisted navigation during surgery according to embodiments of the inventive subject matter will be or become apparent to one with skill in the art upon review of the following drawings and detailed description. It is intended that all such additional systems, computer program products, and methods be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings.

DETAILED DESCRIPTION

Figure 1:
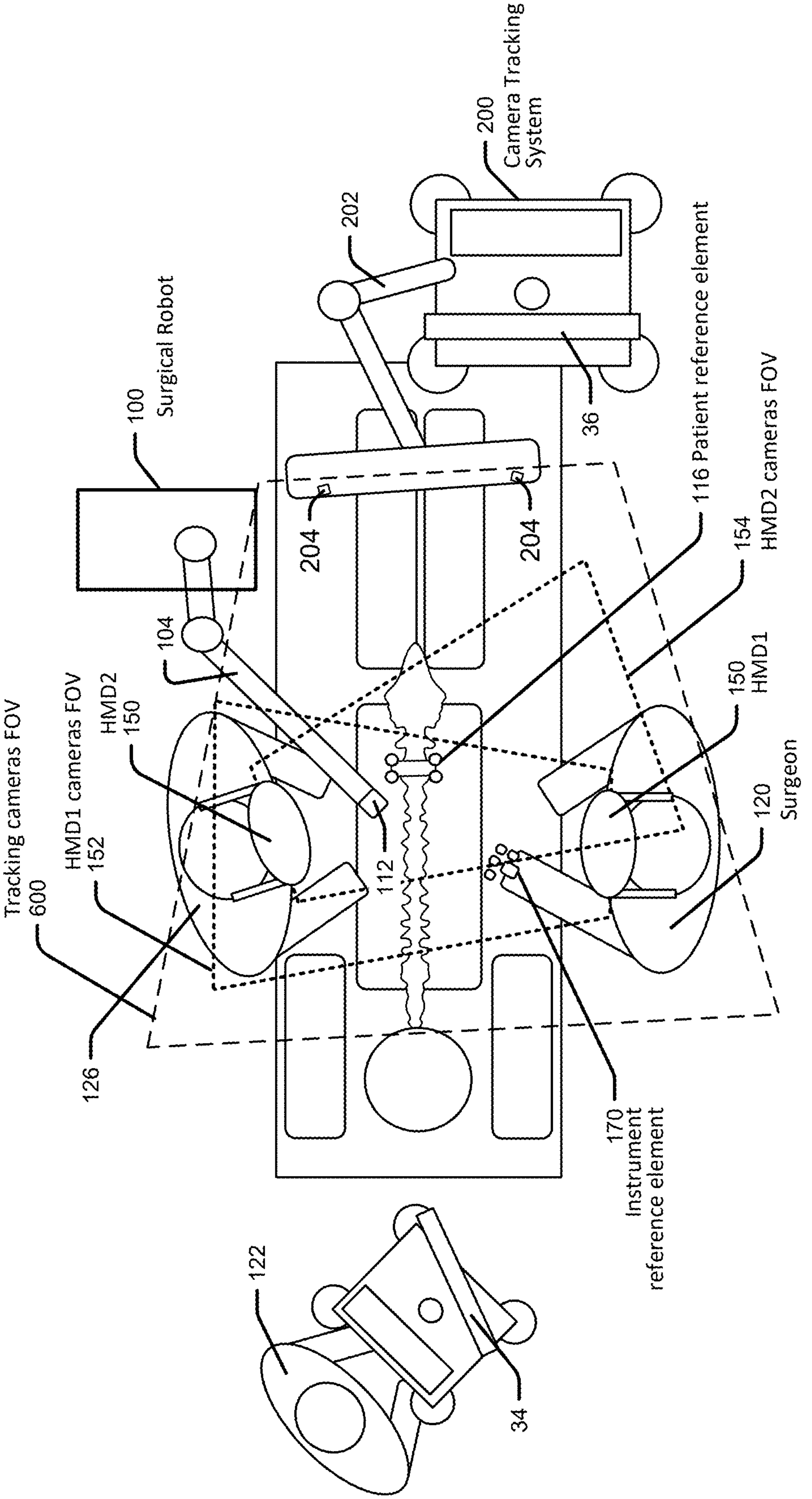
FIG. 1 is an overhead view of a surgical system arranged during a surgical procedure in a surgical room which includes a camera tracking system for computer assisted navigation during surgery and which may further include a surgical robot for robotic assistance according to some embodiments of the present disclosure.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "attached", "supported," and "coupled" and variations thereof are used broadly and encompass both direct and indirect mountings, connections, attachments, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

The present application is related to (1) patent application Ser. No. 15/180,126, filed Jun. 13, 2016 (U.S. Pat. No. 10,842,453), and (2) patent application Ser. No. 15/157,444, filed May 18, 2016 (U.S. Pub. No. 2016/0256225), each of which is incorporated herein by reference.

As noted herein, particular surgical procedures can pose challenges in patient registration, for example, where anatomical features make imaging more challenging and/or where surgical access to such features is limited. One example of such a procedure is total hip arthroplasty (THA), where imaging of the pelvic operating area (or, acetabulum) often includes non-target regions such as the femur.

Certain conventional approaches fail to effectively isolate the acetabulum from non-target regions such as the femur. Further conventional approaches fail to isolate the acetabulum in certain image angles, e.g., in lateral imaging. In particular cases, conventional approaches fail to effectively isolate the acetabulum from non-target regions in merging images of the patient, e.g., in merging pre-operative computed tomography (CT) images with additional (e.g., intra-operative) images or data points.

In contrast to certain of these conventional approaches, a first set of disclosed embodiments includes approaches for registering a patient to a surgical navigation system that are configured to isolate the pelvic operating area (or, acetabulum) from pre-operative CT images. In particular cases, the approaches include identifying and excluding non-target regions from the pre-operative CT images to effectively isolate the acetabulum. Certain approaches include applying a set of rules for identifying non-target areas such as obstructing anatomy (e.g., bone) in the pre-operative CT images. Various approaches apply image-to-image matching to isolate the acetabulum from the non-target area(s). In a first one of these CT image-based approaches, the non-target area is identified using one or more intra-operative fluoroscopy images of the patient. In a second one of these CT image-based approaches, the non-target area is identified using one or more intra-operative point cloud images of the patient.

A second set of disclosed embodiments includes approaches for registering a patient to a surgical navigation system that are configured to isolate the pelvic operating area (or, acetabulum) from multiple fluoroscopy images. Certain of these implementations do not rely on CT images for registering the non-target area. In particular cases, the approaches include identifying and excluding non-target regions from a plurality of fluoroscopy images of the patient to effectively isolate the acetabulum. Certain approaches include applying a set of rules for identifying non-target areas such as obstructing anatomy (e.g., bone) in the fluoroscopy images. Various approaches apply image-to-image matching to isolate the acetabulum from the non-target area(s). In a first one of these fluoroscopy image-based approaches, multiple fluoroscopy images are merged to define distinct planes, from which the target surgical area is located. In a second one of these fluoroscopy image-based approaches, surface painting is used to supplement and/or replace a portion of the fluoroscopy images (e.g., lateral image capture) to locate the target surgical area.

Certain embodiments of the present disclosure include a system for computer assisted navigation during surgery which operates with a navigated ball tip stylus used to contact the surfaces of bones as the stylus travels across the bones. For example, the bones can be continuously contacted by a process known as "surface painting" which refers to the user touching, e.g., tapping, the ball to individual surface locations on the bone, preferably in a zig zag fashion, and/or refer to the user touching and then dragging the ball along, preferably in a zig zag fashion, while maintaining contact with the bone surface while the stylus is tracked to enable definition of an acquired surface of the bone, in accordance with various embodiments disclosed herein. The bones can also be continuously contacted by palpation, i.e., repeatedly lifting and contacting individual surface locations while the navigated ball tip stylus travels, preferably in a zig zag fashion, over the bones. For purposes of the present application, the phrase "painting", "surface painting" and palpating will be used interchangeably to mean contact either by continuous contact or intermittent contact of the bone. Certain aspects of these embodiments are described in further detail in U.S. patent application Ser. No. 18/430,077, filed on Feb. 1, 2024, entitled "Computer Assisted Pelvic Surgery Navigation", the entire contents of which are incorporated by reference herein.

Certain additional embodiments of the present disclosure include a system for computer assisted navigation during surgery which includes a computer platform that is operative to identify a set of locations at which a navigated instrument is palpating a landmark defined on a surface of a pelvic bone of a patient. Certain of these embodiments are described in further detail in U.S. patent application Ser. No. 18/430,077, previously incorporated by reference herein. The computer platform is further operative to determine a center of rotation for a pelvic acetabulum based on the identified set of locations at which the navigated instrument is palpating the landmark, and determine an orientation of an anterior pelvic plane (APP) and/or a functional pelvic plane (FPP) based on the identified set of locations at which the navigated instrument is palpating the landmark and based on the determined center of rotation for the pelvic acetabulum.

Aspects of the disclosed embodiments are discussed below.

Figure 2:
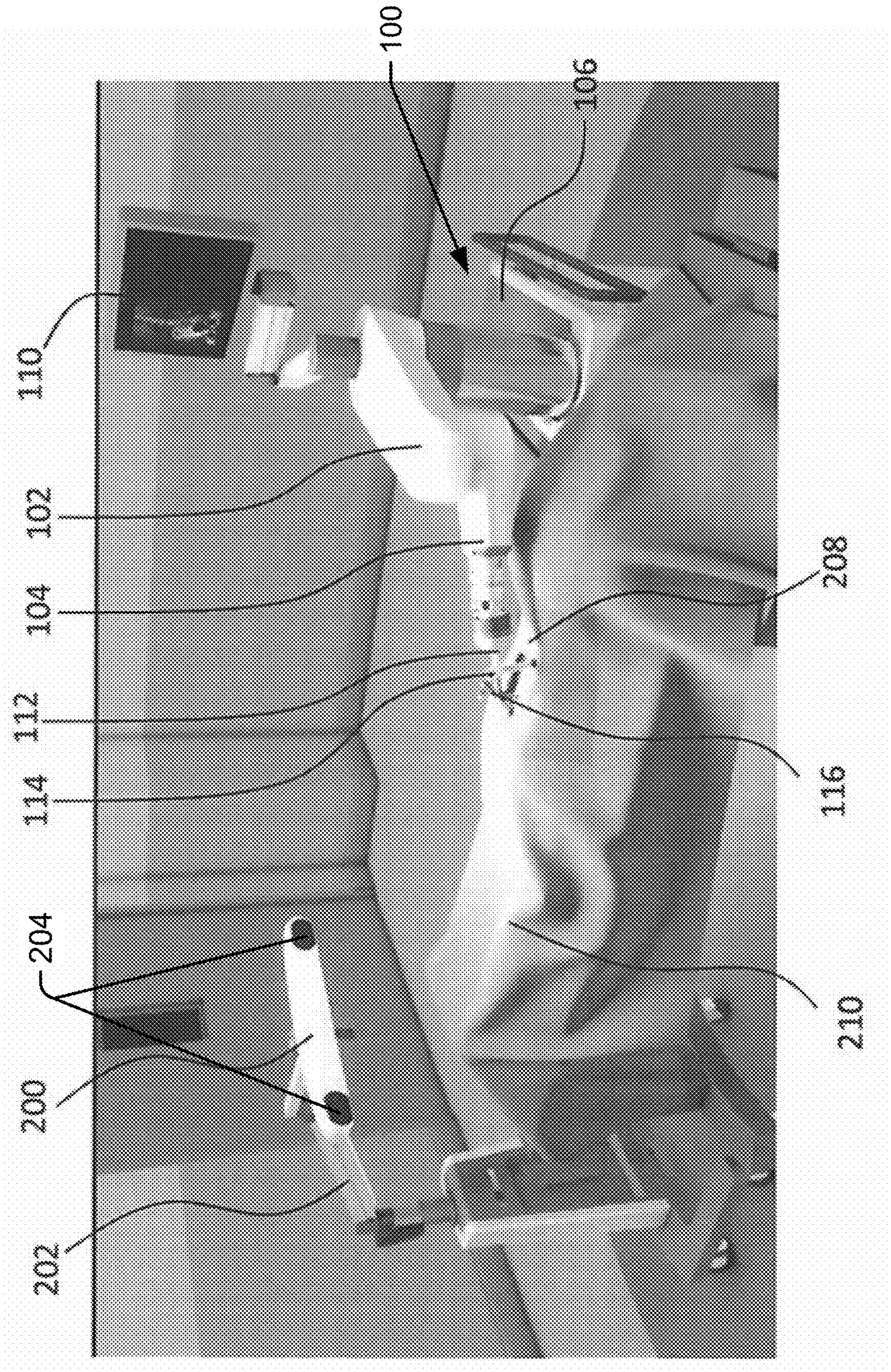
FIG. 2 illustrates the camera tracking system and the surgical robot positioned relative to a patient according to some embodiments of the present disclosure.
Figure 3:
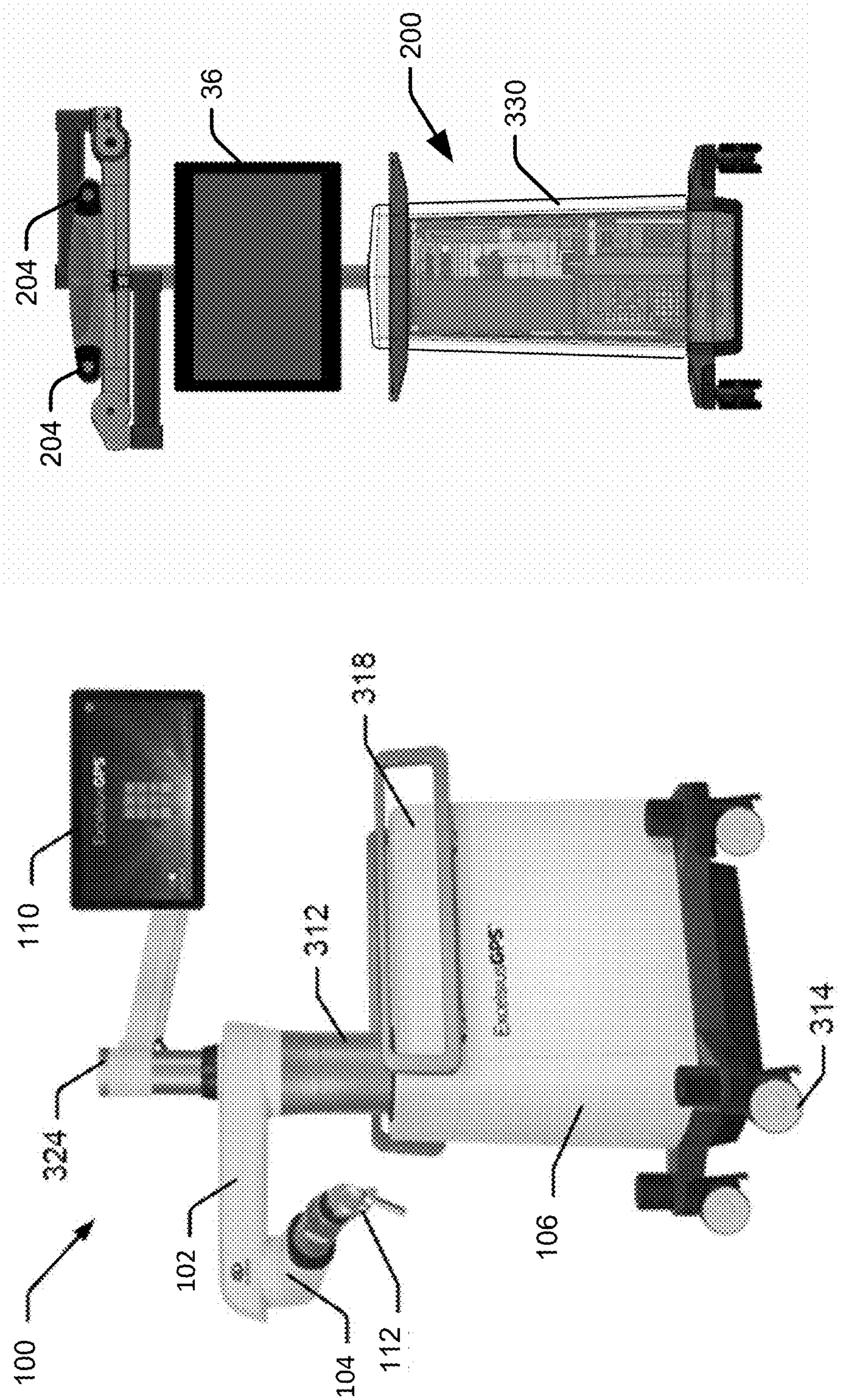
FIG. 3 further illustrates the camera tracking system and the surgical robot configured according to some embodiments of the present disclosure.
Figure 4:
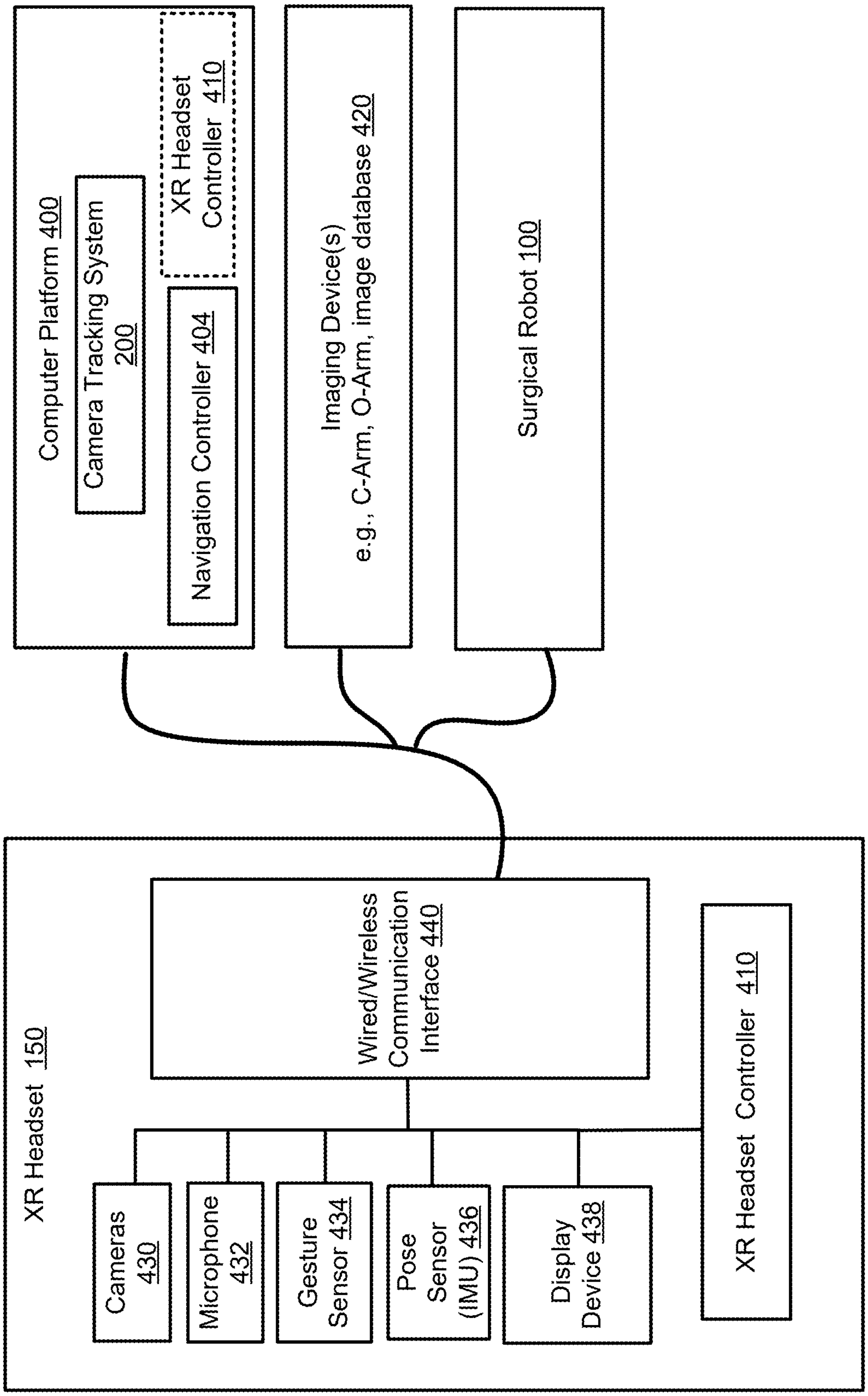
FIG. 4 illustrates a block diagram of a surgical system that includes an extended reality headset, a computer platform, imaging devices, and a surgical robot which are configured to operate according to some embodiments of the present disclosure.

FIG. 1 is an overhead view of a surgical system arranged during a surgical procedure in a surgical room. The system includes a camera tracking system 200 for computer assisted navigation during surgery and may further include a surgical robot 100 for robotic assistance according to some embodiments. FIG. 2 illustrates the camera tracking system 200 and the surgical robot 100 positioned relative to a patient according to some embodiments. FIG. 3 further illustrates the camera tracking system 200 and the surgical robot 100 configured according to some embodiments. FIG. 4 illustrates a block diagram of a surgical system that includes an extended reality (XR) headset 150, a computer platform 400, imaging devices 420, and the surgical robot 100 which are configured to operate according to some embodiments.

The camera tracking system 200, in some cases includes an intraoperative imaging system, that can include distinct imaging modalities, which can include one or more of fluoroscopy, 2D Radiography, and Cone-beam computed tomography (CBCT). Fluoroscopy is a medical imaging technique that shows a continuous X-ray image on a monitor, much like an X-ray movie. 2D Radiography is an imaging technique that uses X-rays to view the internal structure of a non-uniformly composed and opaque object such as the human body. CBCT (or, cone beam 3D imaging) also referred to as C-arm CT, is a medical imaging technique consisting of X-ray computed tomography where the X-rays are divergent, forming a cone. The camera tracking system 200 is capable of: (1) capturing 3-Dimensional (3D) images (e.g., CT, CBCT, MCT, PET, Angiogram, MRI, ultrasound, etc.), (2) capturing 2-Dimensional (2D) images (e.g., fluoroscopy, digital radiography, ultrasound, etc.), and (3) containing an integrated or detachable navigation array having tracking markers (e.g., NIR retroreflective, NIR LED, visible, etc.), which is calibrated to the image space of the 2D and 3D images.

The surgical robot 100 is capable of: (1) using registered 2D and/or 3D images for surgical planning, navigation, and guidance in a variety of workflows (e.g., intraoperative 3D, intraoperative 2D, preoperative 3D to 2D, and intraoperative 3D to 2D, etc.), (2) containing a camera tracking system 200 capable of tracking markers (e.g., NIR retroreflective, NIR LED, visible, etc.). In some cases, as noted herein, a patient reference array (DRB 116) is (1) capable of rigidly attaching to the patient anatomy, and (2) contains an array of tracking markers (e.g., NIR retroreflective, NIR LED, visible, etc.).

The XR headsets 150 may be configured to augment a real-world scene with computer generated XR images while worn by personnel in the operating room. The XR headsets 150 may be configured to provide an augmented reality (AR) viewing environment by displaying the computer generated XR images on a see-through display screen that allows light from the real-world scene to pass therethrough for combined viewing by the user. Alternatively, the XR headsets 150 may be configured to provide a virtual reality (VR) viewing environment by preventing or substantially preventing light from the real-world scene from being directly viewed by the user while the user is viewing the computer-generated AR images on a display screen. The XR headsets 150 can be configured to provide both AR and VR viewing environments. Thus, the term XR headset can referred to as an AR headset or a VR headset.

Referring to FIGS. 1-4, the surgical robot 100 may include, for example, one or more robot arms 104, a display 110, an end-effector 112, for example, including a guide tube 114, and an end effector reference element which can include one or more tracking fiducials. A patient reference element 116 (DRB) has a plurality of tracking fiducials and is secured directly to the patient 210 (e.g., to a bone of the patient such as a pelvis, femur or tibia). A reference element 170 is attached to or formed on an instrument, surgical tool, surgical implant device, etc.

The camera tracking system 200 includes tracking cameras 204 which may be spaced apart to provide stereo cameras configured with partially overlapping fields-of-view. The camera tracking system 200 can have any suitable configuration of arm(s) 202 to move, orient, and support the tracking cameras 204 in a desired location, and may contain at least one processor operable to track the location of an individual fiducial and pose of an array of fiducials of a reference element.

As used herein, the term "pose" refers to the location (e.g., along 3 orthogonal axes) and/or the rotation angle (e.g., about the 3 orthogonal axes) of fiducials (e.g., DRB) relative to another fiducial (e.g., surveillance fiducial) and/or to a defined coordinate system (e.g., camera coordinate system, navigation coordinate system, etc.). A pose may therefore be defined based on only the multidimensional location of the fiducials relative to another fiducial and/or relative to the defined coordinate system, based on only the multidimensional rotational angles of the fiducials relative to the other fiducial and/or to the defined coordinate system, or based on a combination of the multidimensional location and the multidimensional rotational angles. The term "pose" therefore is used to refer to location, rotational angle, or combination thereof of, e.g., an instrument reference element 170, a patient reference element 116, or the like.

The tracking cameras 204 may include, e.g., infrared cameras (e.g., bifocal or stereophotogrammetric cameras) operable to identify, for example, active and passive tracking fiducials for single fiducials (e.g., a surveillance fiducial) and reference elements which can be formed on or attached to the patient 210 (e.g., patient reference element 116, DRB, etc.), end effector 112 (e.g., end effector reference element), XR headset(s) 150 worn by a surgeon 120 and/or a surgical assistant 126, etc. in a given measurement volume of a camera coordinate system while viewable from the perspective of the tracking cameras 204. The tracking cameras 204 may scan the given measurement volume and detect light that is emitted or reflected from the fiducials in order to identify and determine locations of individual fiducials and poses of the reference elements in three-dimensions. For example, active reference elements may include infrared-emitting fiducials that are activated by an electrical signal (e.g., infrared light emitting diodes (LEDs)), and passive reference elements may include retro-reflective fiducials that reflect infrared light (e.g., they reflect incoming IR radiation into the direction of the incoming light), for example, emitted by illuminators on the tracking cameras 204 or other suitable device.

The XR headsets 150 may each include tracking cameras (e.g., spaced apart stereo cameras) that can track the location of a surveillance fiducial and poses of reference elements within the XR camera headset fields-of-view (FOVs) 152 and 154, respectively. Accordingly, as illustrated in FIG. 1, the location of the surveillance fiducial and the poses of reference elements on various objects can be tracked while in the FOVs 152 and 154 of the XR headsets 150 and/or a FOV 600 of the tracking cameras 204.

FIGS. 1 and 2 illustrate a potential configuration for the placement of the camera tracking system 200 and the surgical robot 100 in an operating room environment. Computer assisted navigated surgery can be provided by the camera tracking system 200 controlling the XR headsets 150 and/or other displays 34, 36, and 110 to display surgical procedure navigation information. The surgical robot 100 is optional during computer assisted navigated surgery.

The camera tracking system 200 may operate using tracking information and other information provided by multiple XR headsets 150 such as inertial tracking information and optical tracking information (frames of tracking data). The XR headsets 150 operate to display visual information and may play-out audio information to the wearer. This information can be from local sources (e.g., the surgical robot 100), imaging devices 420 (FIG. 4), remote sources (e.g., patient medical image database), and/or other electronic equipment. The camera tracking system 200 may track fiducials in 6 degrees-of-freedom (6 DOF) relative to three axes of a 3D coordinate system and rotational angles about each axis. The XR headsets 150 may also operate to track hand poses and gestures to enable gesture-based interactions with "virtual" buttons and interfaces displayed through the XR headsets 150, and can also interpret hand or finger pointing or gesturing as various defined commands. Additionally, the XR headsets 150 may have a 1-10× magnification digital color camera sensor called a digital loupe. In some embodiments, one or more of the XR headsets 150 are minimalistic XR headsets that display local or remote information but include fewer sensors and are therefore more lightweight.

An "outside-in" machine vision navigation bar supports the tracking cameras 204 and may include a color camera. The machine vision navigation bar generally has a more stable view of the environment because it does not move as often or as quickly as the XR headsets 150 while positioned on wearers' heads. The patient reference element 116 (DRB) is generally rigidly attached to the patient 210 with stable pitch and roll relative to gravity. This local rigid patient reference 116 can serve as a common reference for reference frames relative to other tracked elements, such as a reference element on the end effector 112, instrument reference element 170, and reference elements on the XR headsets 150.

In some embodiments, at the end of the end effector 112, instruments are connected to perform operations such as resection, reaming, broaching, drilling and screw placement.

When present, the surgical robot 100 (also "robot") may be positioned near or next to patient 210. The robot 100 can be positioned at any suitable location near the patient 210 depending on the area of the patient 210 undergoing the surgical procedure. The camera tracking system 200 may be separate from the robot system 100 and positioned at the foot of patient 210. This location allows the tracking camera 200 to have a direct visual line of sight to the surgical area 208 (FIG. 2). In the configuration shown in FIG. 1, the surgeon 120 may be positioned across from the robot 100, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. An anesthesiologist 122, nurse or scrub tech can operate equipment which may be connected to display information from the camera tracking system 200 on a display 34.

With respect to the other components of the robot 100, the display 110 can be attached to the surgical robot 100 or in a remote location. End-effector 112 may be coupled to the robot arm 104 and controlled by at least one motor. In some embodiments, end-effector 112 includes a guide tube 114, which is configured to receive and orient a surgical instrument, tool, or implant used to perform a surgical procedure on the patient 210. In some other embodiments, the end-effector 112 includes a passive structure guiding a saw blade (e.g., sagittal saw) along a defined cutting plane.

As used herein, the term "end-effector" is used interchangeably with the terms "end-effectuator" and "effectuator element." The term "instrument" is used in a non-limiting manner and can be used interchangeably with "tool" and "implant" to generally refer to any type of device that can be used during a surgical procedure in accordance with embodiments disclosed herein. The more general term device can also refer to structure of the end-effector, etc. Example instruments, tools, and implants include, without limitation, drills, screwdrivers, saws, dilators, retractors, probes, implant inserters, and implant devices such as screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument in a desired manner.

The surgical robot 100 is operable to control the translation and orientation of the end-effector 112. The robot 100 may move the end-effector 112 under computer control along x-, y-, and z-axes, for example. The end-effector 112 can be configured for selective rotation about one or more of the x-, y-, and z-axes, and a Z Frame axis, such that one or more of the Euler Angles (e.g., roll, pitch, and/or yaw) associated with end-effector 112 can be selectively computer controlled. In some embodiments, selective control of the translation and orientation of end-effector 112 can permit performance of medical procedures with significantly improved accuracy compared to conventional robots that utilize, for example, a 6 DOF robot arm comprising only rotational axes. For example, the surgical robot 100 may be used to operate on patient 210, and robot arm 104 can be positioned above the body of patient 210, with end-effector 112 selectively angled relative to the z-axis toward the body of patient 210.

In some example embodiments, the XR headsets 150 can be controlled to dynamically display an updated graphical indication of the pose of the surgical instrument so that the user can be aware of the pose of the surgical instrument at all times during the procedure.

In some further embodiments, surgical robot 100 can be operable to correct the path of a surgical instrument guided by the robot arm 104 if the surgical instrument strays from the selected, preplanned trajectory. The surgical robot 100 can be operable to permit stoppage, modification, and/or manual control of the movement of end-effector 112 and/or the surgical instrument. Thus, in use, a surgeon or other user can use the surgical robot 100 as part of computer assisted navigated surgery, and has the option to stop, modify, or manually control the autonomous or semi-autonomous movement of the end-effector 112 and/or the surgical instrument.

Fiducials of reference elements can be formed on or connected to robot arms 102 and/or 104, the end-effector 112 (e.g., end-effector element 114 in FIG. 2), and/or a surgical instrument (e.g., instrument element 170) to enable tracking of poses in a defined coordinate system, e.g., such as in 6 DOF along 3 orthogonal axes and rotation about the axes. The reference elements enable each of the marked objects (e.g., the end-effector 112, the patient 210, and the surgical instruments) to be tracked by the tracking camera 200, and the tracked poses can be used to provide navigated guidance during a surgical procedure and/or to control movement of the surgical robot 100 for guiding the end-effector 112 and/or an instrument manipulated by the end-effector 112.

Referring to FIG. 3 the surgical robot 100 may include a display 110, upper arm 102, lower arm 104, end-effector 112, vertical column 312, casters 314, a table 318, and ring 324 which uses lights to indicate statuses and other information. Cabinet 106 may house electrical components of surgical robot 100 including, but not limited to, a battery, a power distribution module, a platform interface board module, and a computer. The camera tracking system 200 may include a display 36, tracking cameras 204, arm(s) 202 (FIG. 1), a computer housed in cabinet 330, and other components.

In computer assisted navigated surgeries, perpendicular 2D scan slices, such as axial, sagittal, and/or coronal views of patient anatomical structure are displayed to enable user visualization of the patient's anatomy alongside the relative poses of surgical instruments. An XR headset or other display can be controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.

Example Surgical System:

FIG. 4 illustrates a block diagram of a surgical system that includes an XR headset 150, a computer platform 400, imaging devices 420, and a surgical robot 100 which are configured to operate according to some embodiments.

The imaging devices 420 may include a C-arm imaging device, an O-arm imaging device, other imaging device, and/or a patient image database of 2D and/or 3D images. The XR headset 150 provides an improved human interface for performing navigated surgical procedures. The XR headset 150 can be configured to provide functionalities, e.g., via the computer platform 400, that include without limitation any one or more of: identification of hand gesture based commands, display XR graphical objects on a display device 438 of the XR headset 150 and/or another display device. The display device 438 may include a video projector, flat panel display, etc. The user may view the XR graphical objects as an overlay anchored to particular real-world objects viewed through a see-through display screen. The XR headset 150 may additionally or alternatively be configured to display on the display device 438 video streams from cameras mounted to one or more XR headsets 150 and other cameras.

Electrical components of the XR headset 150 can include a plurality of cameras 430, a microphone 432, a gesture sensor 434, a pose sensor (e.g., inertial measurement unit (IMU)) 436, the display device 438, and a wireless/wired communication interface 440. The cameras 430 of the XR headset 150 may be visible light capturing cameras, near infrared capturing cameras, or a combination of both.

The cameras 430 may be configured to operate as the gesture sensor 434 by tracking for identification user hand gestures performed within the field-of-view of the camera(s) 430. Alternatively, the gesture sensor 434 may be a proximity sensor and/or a touch sensor that senses hand gestures performed proximately to the gesture sensor 434 and/or senses physical contact, e.g., tapping on the sensor 434 or its enclosure. The pose sensor 436, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, a surgical system includes the camera tracking system 200 which may be connected to a computer platform 400 for operational processing and which may provide other operational functionality including a navigation controller 404 and/or an XR headset controller 410. The surgical system may further include the surgical robot 100. The navigation controller 404 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 200. The navigation controller 404 may be further configured to generate navigation information based on a target pose for a surgical tool, a pose of the anatomical structure, and a pose of the surgical tool and/or an end effector 112 of the surgical robot 100. The navigation information may be displayed through the display device 438 of the XR headset 150 and/or another display device to indicate where the surgical tool and/or the end effector 112 of the surgical robot 100 should be moved to perform a surgical procedure according to a defined surgical plan.

The electrical components of the XR headset 150 can be operatively connected to the electrical components of the computer platform 400 through the wired/wireless interface 440. The electrical components of the XR headset 150 may be operatively connected, e.g., through the computer platform 400 or directly connected, to various imaging devices 420, e.g., the C-arm imaging device, the O-arm imaging device, other imaging device, the patient image database, and/or to other medical equipment through the wired/wireless interface 440.

The surgical system may include a XR headset controller 410 that at least partially resides in the XR headset 150, the computer platform 400, and/or another system component connected via wired cables and/or wireless communication links. Various functionality may be provided by software executed by the XR headset controller 410. The XR headset controller 410 is configured to receive information from the camera tracking system 200 and the navigation controller 404, and to generate an XR image based on the information for display on the display device 438.

The XR headset controller 410 can be configured to operationally process frames of tracking data from the cameras 430 (tracking cameras), signals from the microphone 432, and/or information from the pose sensor 436 and the gesture sensor 434, to generate information for display as XR images on the display device 438 and/or for display on other display devices for user viewing. Thus, the XR headset controller 410 as illustrated as a circuit block within the XR headset 150 is to be understood as being operationally connected to other illustrated components of the XR headset 150 but not necessarily residing within a common housing or being otherwise transportable by the user. For example, the XR headset controller 410 may additionally or alternatively reside within the computer platform 400 which, in turn, may reside within the cabinet 330 of the camera tracking system 200, the cabinet 106 of the surgical robot 100, etc.

Bone Surface Acquisition Through Palpation ("Painting") Using Ball Tip Stylus:

Various embodiments are directed to registering patient anatomy in an algorithm for computer assisted navigation during surgery through the acquisition of particular landmarks on bones using a process of palpating the surface of the bones with a tracked ball tip stylus. The location of a bone landmark may be acquired and registered by a single touch of the tracked ball tip stylus. A surface of the bone may be acquired and registered by multiple individual touches of, e.g., tapping, the tracked ball tip stylus and/or by touching and then maintaining contact with the surface while moving the ball along the surface, e.g., "painting" the surface being tracked. Defined landmarks (e.g. most distal and posterior points) can be extracted and other measurements of the bone surface can be performed and concurrently registered for computer assisted navigation. The surface of the bone can be defined (recreated) based on a cloud of points collected by moving the ball of the tracked ball tip stylus on a surface of the bone.

Figure 5:
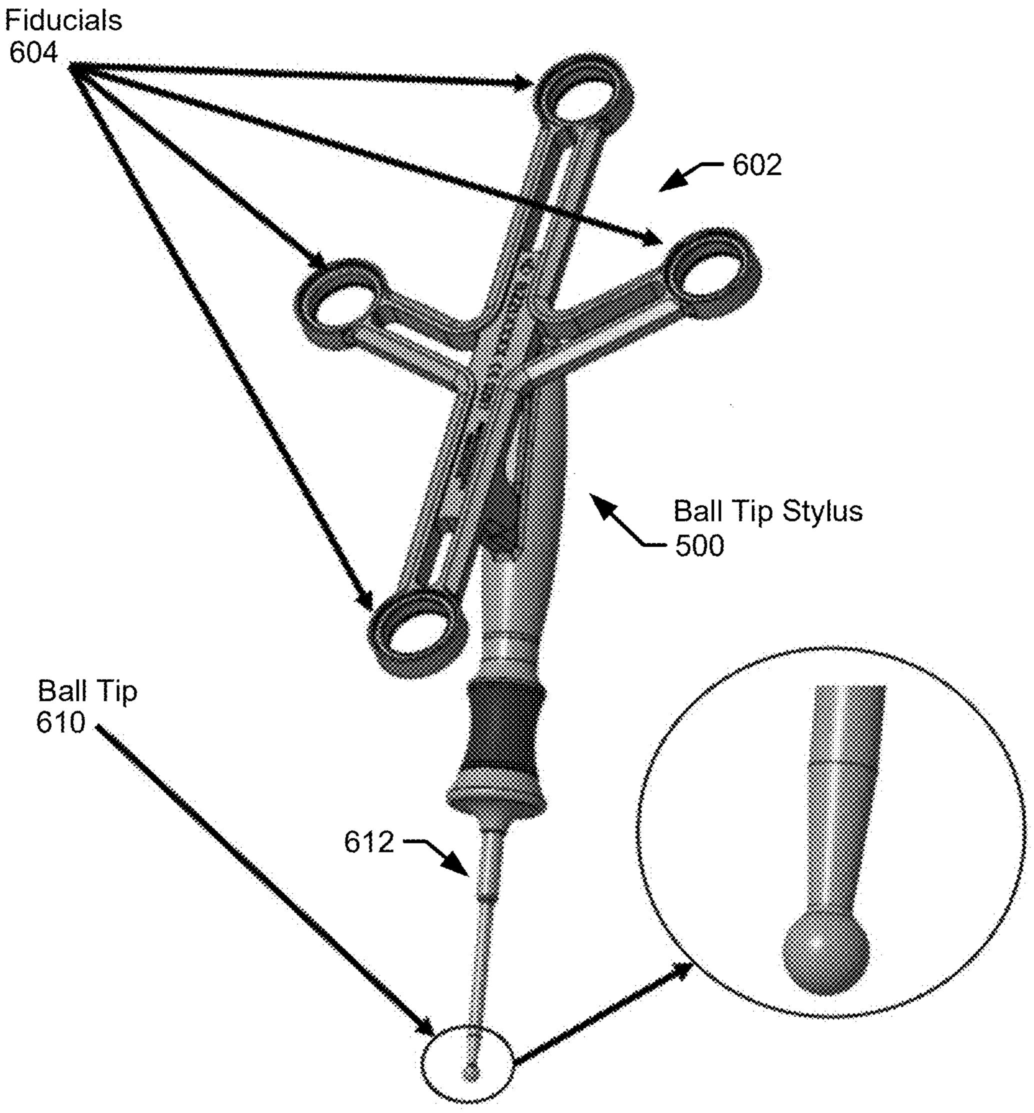
FIG. 5 illustrates the ball tip stylus configured in accordance with some embodiments of the present disclosure.

FIG. 5 illustrates a ball tip stylus 500 configured in accordance with some embodiments of the present disclosure. Referring to FIG. 5, the ball tip stylus 500 includes a ball 610 at a tip that is connected through an interconnecting member 612 to a reference element 602 having an array of fiducials 604. The fiducials 604 may be any shape, such as disks, spheres, etc., may be any color, and may be passive to reflect light or active to emit light.

Tip shape can have a considerable influence on how easy and precise it is for a user to move the tip across a bone. It has been determined that a ball (spherical) tip 610 glides more easily and consistently on the bone surface but requires taking into account the radius of the tip when defining a location of the surface. The bigger the ball radius is, the easier the gliding capabilities are, but the more difficult it is to access certain areas of bones of a patient, for example acetabular cartilage or acetabular fossa of a pelvis.

The user, e.g., surgeon, can manipulate the ball 610 of the ball tip stylus 500 to sweep the surface of the bone or cartilage. Doing so, the camera tracking system 200 can measure the location of the ball 610 in a continuous operation and output a cloud of location points. Alternatively, the user can subsequently measure a sufficient amount of points by touching the location points one-by-one with the ball 610 of the ball tip stylus 500 being tracked by the camera tracking system 200.

Figure 6:
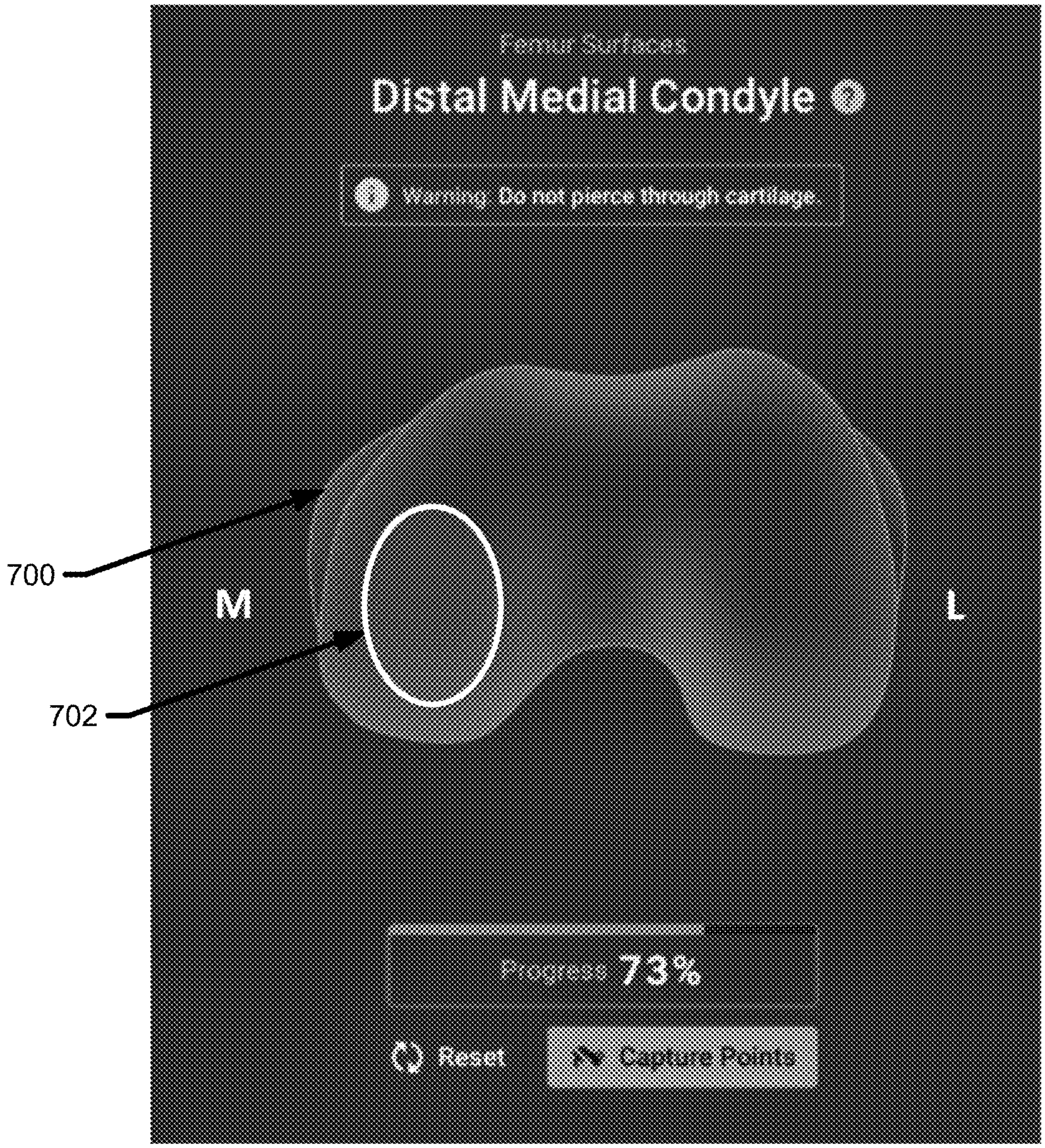
FIG. 6 illustrates a user interface displayed to guide a user through registration of condylar surfaces by palpation using the ball tip stylus in accordance with some embodiments of the present disclosure.

The user may be guided by displayed and/or audible instructions generated by a software application, e.g., algorithm for computer assisted navigation, to acquire a defined surface area of bone(s). FIG. 6 illustrates a user interface that is displayed on a display device to guide a user through registration of condylar surfaces 700 by palpation using the ball tip stylus 500 in accordance with some embodiments of the present disclosure. While condylar surfaces are illustrated with reference to FIG. 6, it should be noted that similar processes can be performed and similar information can be determined/identified with regards to, e.g., a pelvis or other bone or anatomical structure of a patient.

The user interface displays one or more indicia 702 to indicate that the user should use the ball tip stylus 500 to palpate the distal medial condyle to cause the system to define a surface of the distal medial condyle and register the surface in an algorithm for computer assisted navigation during surgery.

The locations (points) acquired by the camera tracking system 200 correspond to the center of the ball 610 during the acquisition by the user. The locations can be used to define an offset-acquired surface of the bone. The offset-acquired surface can then be translated to correspond to the actual surface of the bone based on the radius of the ball 610. The system may use a surface matching algorithm for some of these operations.

Figure 7:
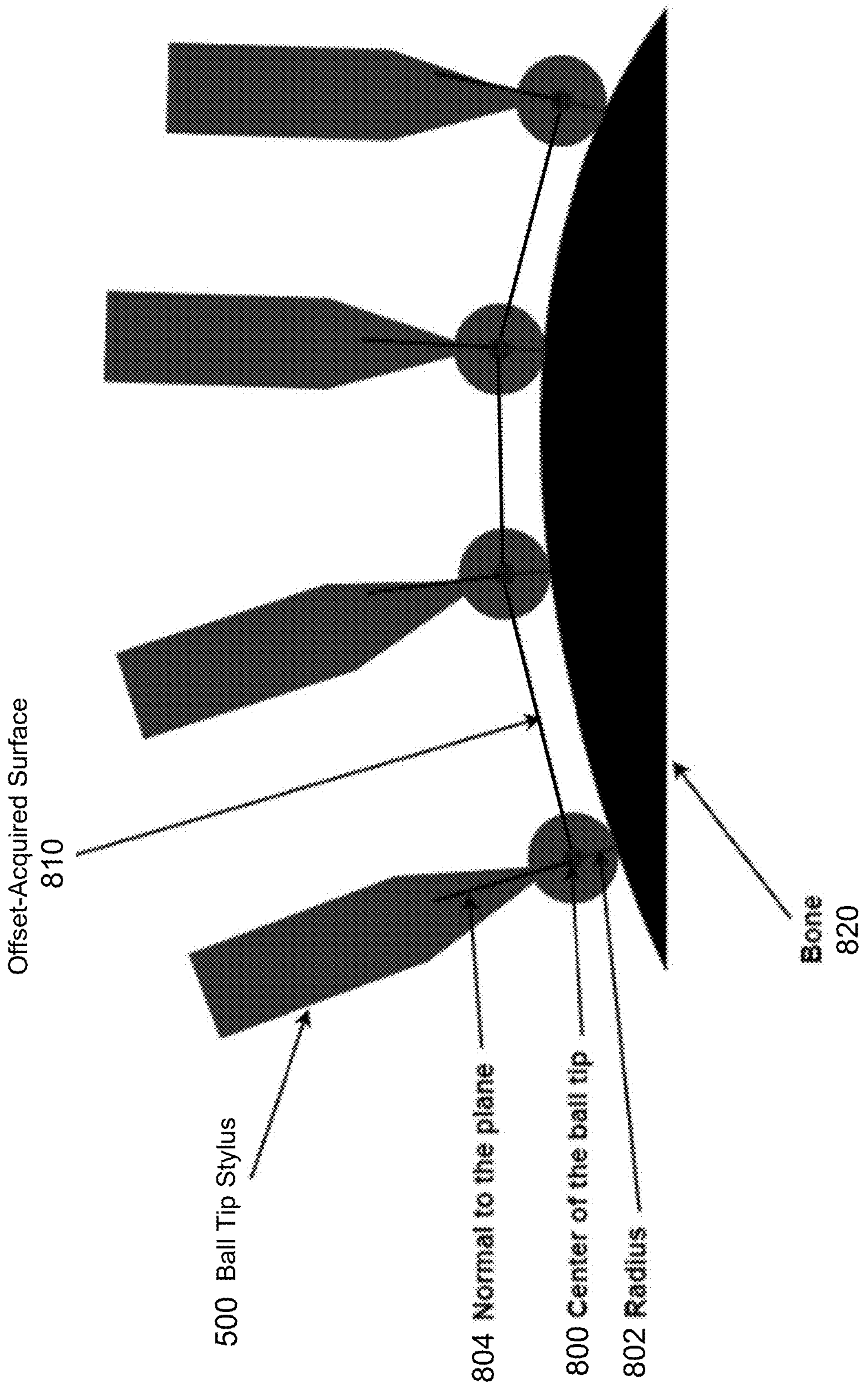
FIG. 7 illustrates a schematic view of operations for defining and then translating an offset-acquired surface of a bone toward the surface of the bone along local normal vectors based on a radius of the ball to define an acquired surface of the bone in accordance with some embodiments of the present disclosure.

FIG. 7 illustrates a schematic view of operations for defining and then translating an offset-acquired surface 810 of a bone 820 toward the surface of the bone 820 along local normal vectors based on a radius of the ball 610 to define an acquired surface of the bone 820 in accordance with some embodiments of the present disclosure. Referring to FIG. 7, in one illustrative embodiment the operations include acquiring locations of the center 800 of the ball 610 as it is used to palpate a surface of the bone 820. The locations of the center 800 of the ball 610 are then mathematically connected together to define an offset-acquired surface 810 of the bone 820, which is offset from the real bone surface by a distance corresponding to the radius 802 of the ball 610. To match the offset-acquired surface 810 to the surface of bone 820, the operations determine the local normal vector to the real bone surface for each acquired location of the center 800 of the ball 610. The operations then translate each acquired location of the center 800 of the ball 610 along the normal vector toward the bone 820 by a distance corresponding to the radius 802 of the ball 610. These operations enable the surface to be defined in a manner agnostic to the orientation of the ball tip stylus 500, e.g., when not perpendicular to the palpated surface. The acquired surface 810 of the bone, corresponding to the real bone surface, can then be defined by mathematically connecting together the translated locations.

Landmarks relevant for the surgical procedure (e.g., most posterior condylar points and most distal condylar points for femur, most distal points on the plateaux for tibia, etc.) can be extracted for planning and executing computer assisted navigation. Based on the acquired surface 810 (FIG. 7), a registration algorithm can then match patient anatomy with a 3D model of the bone and/or identify additional landmarks for use in planning and executing computer assisted navigation.

These operations can be more generalized in accordance with some embodiments. Example approaches for identifying locations of fiducials 604 and registering a patient based on offset-acquired surfaces 810 is further described in U.S. patent application Ser. No. 18/430,077, previously incorporated by reference herein. For example, in certain operational approaches, as described in U.S. patent application Ser. No. 18/430,077, two steps of acquisition are used. In one step, landmarks on the anterior and distal surfaces of femur are acquired and partial registration of the femur is performed, and acquisition of the tibial plateau and full registration of the tibia is performed. Tibial resection is performed. Then, in a second acquisition step, acquisition of the posterior surface of the femoral condyles is performed. This operational approach may be adapted for use in other arthroplasty procedures as will be understood by one having skill in the art.

In further embodiments, the systems and embodiments discussed above (along with additional/alternative embodiments discussed below) are used to assist in total hip arthroplasty (THA) surgery. For example, the systems and embodiments may be used to prepare the bones (e.g., pelvis acetabulum and femur) and place corresponding implants in the patient.

Certain landmarks and/or planes may be useful in registering or determining the orientation of a patient in 3D space of the operating room. For example, as part of a computer assisted navigation workflow during surgery, the system can register or determine an orientation of an anterior pelvic plane (APP) and/or a functional pelvic plane (FPP) of the patient to determine orientation of the patient on an operating room table during total hip arthroplasty (THA) surgery.

The system may provide computer assisted navigation throughout the entire spectrum of care (pre-operative, intra-operative and post-operative). Accordingly, the system can be configured to perform multiple workflows. Some workflows use scans of the patient (X-ray, Computerized Tomography (CT)) obtained during a pre-operative step.

Example Imageless Workflow

In some embodiments of the present disclosure, the system performs an imageless workflow in which no pre-operative images are used. Information about the patient anatomy in the operating room (OR) can be obtained by the surgeon measuring key parameters of the patient's bone using the system as described herein. For example, a computer platform of the system operates to identify location of landmarks (e.g., points, axes, and/or surfaces) on the bone and register the locations either concurrently with the identification or thereafter. The locations can be used to define reference plane(s) (e.g., APP and/or FPP) which, in turn, are used to plan implants and navigate the robot and surgical instruments for THA surgical procedures.

In some embodiments, the only pre-operative use case associated with the imageless workflow may be the initial patient assessment. The surgeon may assess the patient's mobility and health status with assistance from sensors (e.g., sensors made by Globus Medical which are attached to the leg), physical exercises, and/or clinical surveys to determine if THA is recommended. Gathered data may then be stored and processed by the system before being analyzed by the surgeon to facilitate a final decision. Subsequently, the data may be reused by an application (e.g., surgery planning application by Globus Medical) to establish the most appropriate implant surgical plan.

Figure 8:
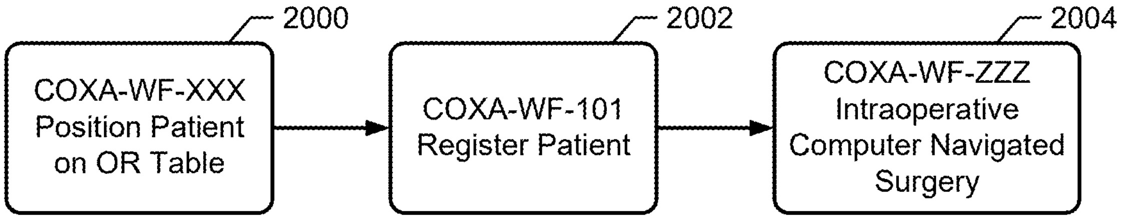
FIG. 8 illustrates a flowchart of an imageless workflow during an intra-operative portion of a total hip arthroplasty (THA) surgery, in accordance with some embodiments of the present disclosure.

FIG. 8 illustrates a flowchart for an imageless workflow during an intra-operative portion of a THA surgery, in accordance with some embodiments of the present disclosure.

In some embodiments, after positioning the patient on the operating room table (step 2000), some of the operations discussed above and below may be performed during step 2002 to register a patient and before another step 2004 for intraoperative computer navigated surgery. In the case of a hip, a pelvis or acetabulum of the patient is registered in the tracking coordinate system of the camera tracking system 200. As shown in FIG. 1, the pelvis or acetabulum is registered in the optical coordinate system. In one embodiment, the registration is done in an imageless modality without the use of any medical images such as X-rays or CT images from an imaging device. As noted herein, in other embodiments, registration is performed using one or more pre-operative X-ray images and/or CT images.

Figure 9:
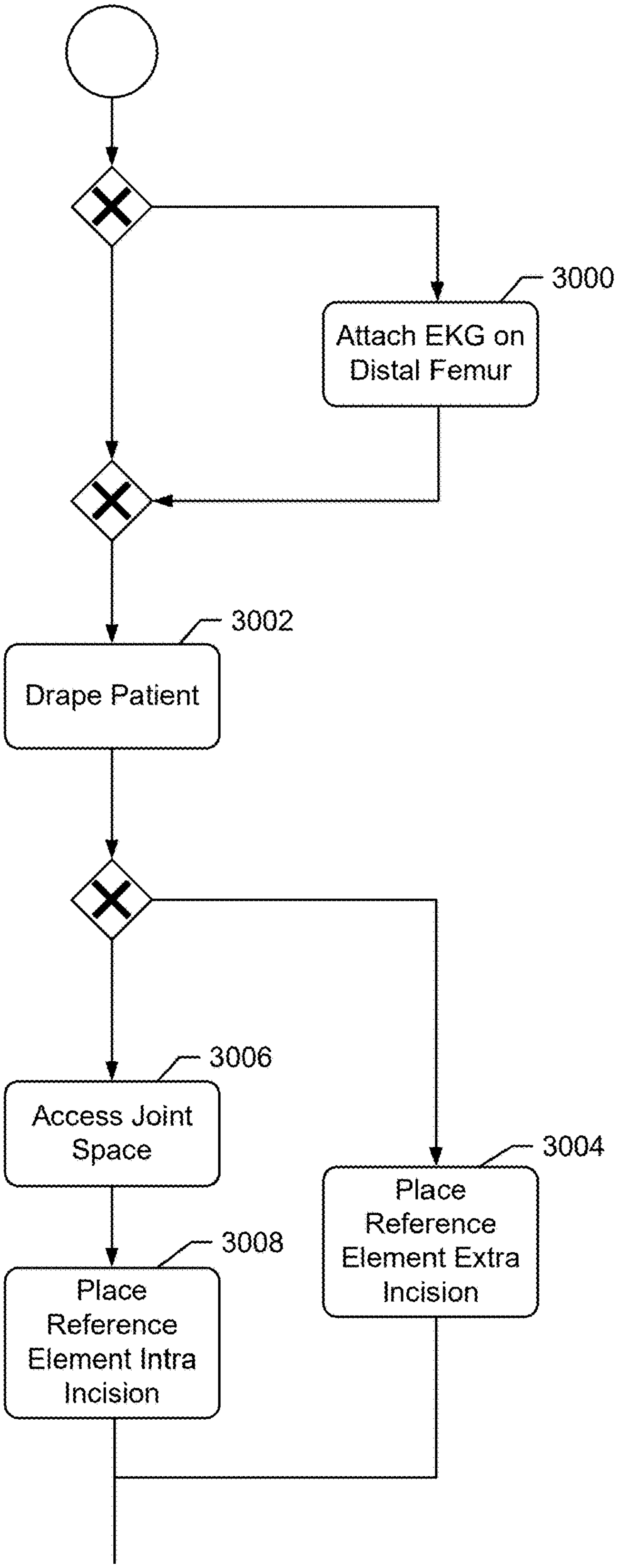
FIG. 9 illustrates a flowchart of a patient preparation process before registration, in accordance with some embodiments of the present disclosure.

FIG. 9 illustrates a flowchart of a patient preparation process before registration, in accordance with some embodiments of the present disclosure.

The patient preparation process may begin with a patient being positioned in a lateral or supine position on the OR table. The patient's body is prepared for registration. Optionally, in step 3000, an EKG/ECG patch electrode is attached on or adjacent a distal end of the patient's femur. The EKG/ECG patch electrode may be placed on the center of the patella or slightly inferior to the center. In some embodiments, the patch location is in line with the anatomic axis of the femur. This patch may be used to acquire the most distal point of the femur under the drape at a later stage. This patch may also be used to track the femur in space (e.g., when the patient's leg is moved during surgery) and may also be used to assist in measuring the patient's leg length. However, in some embodiments, this operation (step 3000) is skipped.

In some embodiments, the EKG/ECG patch electrode includes an adhesive patch that is removably attachable to the patient. In some embodiments, the patch may be black or dark to be more visible to the tracking camera. In other embodiments, the patch and patch electrodes are not visible by the tracking camera as they are under a drape. The patch geometry (like a nipple) will help the surgeon to always touch a single point on or adjacent the distal part of the femur (anterior patella region) with a navigated stylus/instrument which is trackable by the tracking camera. This ensures that the surgeon always collects the same point to measure the leg length or medio-lateral offset.

In step 3002, the patient body is draped. Then, depending on the surgeon's technique, the navigated pelvis Dynamic Reference Base (DRB) marker array (also referred herein as a reference element) is placed intra-incision (steps 3006-3008) or extra-incision (step 3004) with the help of cortical pins drilled into the pelvic bone. In some embodiments, the DRB is oriented to be visible by the tracking camera(s) (e.g., a stereoscopic tracking camera) installed on the camera tracking system (e.g., camera tracking system 200 of FIG. 1) or the headset (e.g., XR headset 150 of FIG. 1).

In one embodiment, the operation to place the reference element intra-incision, includes using the system to track and navigate access to the joint space (step 3006) and placing the reference element intra-incision. In an alternative embodiment, the reference element is placed extra-incision (step 3004) and the system does not necessarily need to be used to track and navigate access to the joint space.

After the reference element has been placed intra-incision or extra-incision, data points and axes can be collected on the patient anatomy with the assistance of navigated instruments and using the pelvis DRB coordinate system as a spatial reference. In addition to this, two pelvic reference planes can be established to plan placement of implants by measuring angular deviations such as inclination and version of the acetabular cup implant as shown in FIGS. 10A-10B.

Figure 10A:
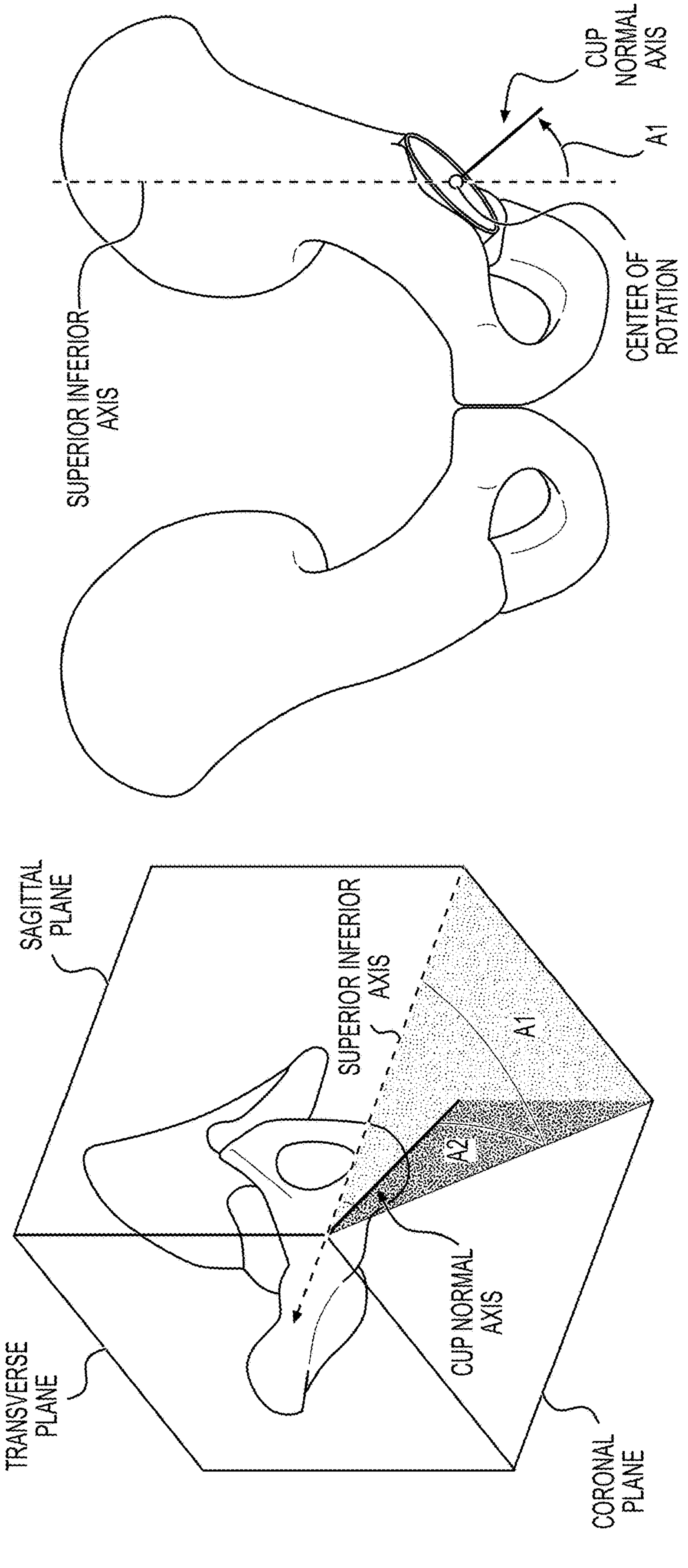
FIG. 10A illustrates a radiographic inclination angle measured in the coronal plane of the patient, in accordance with some embodiments of the present disclosure.
Figure 10B:
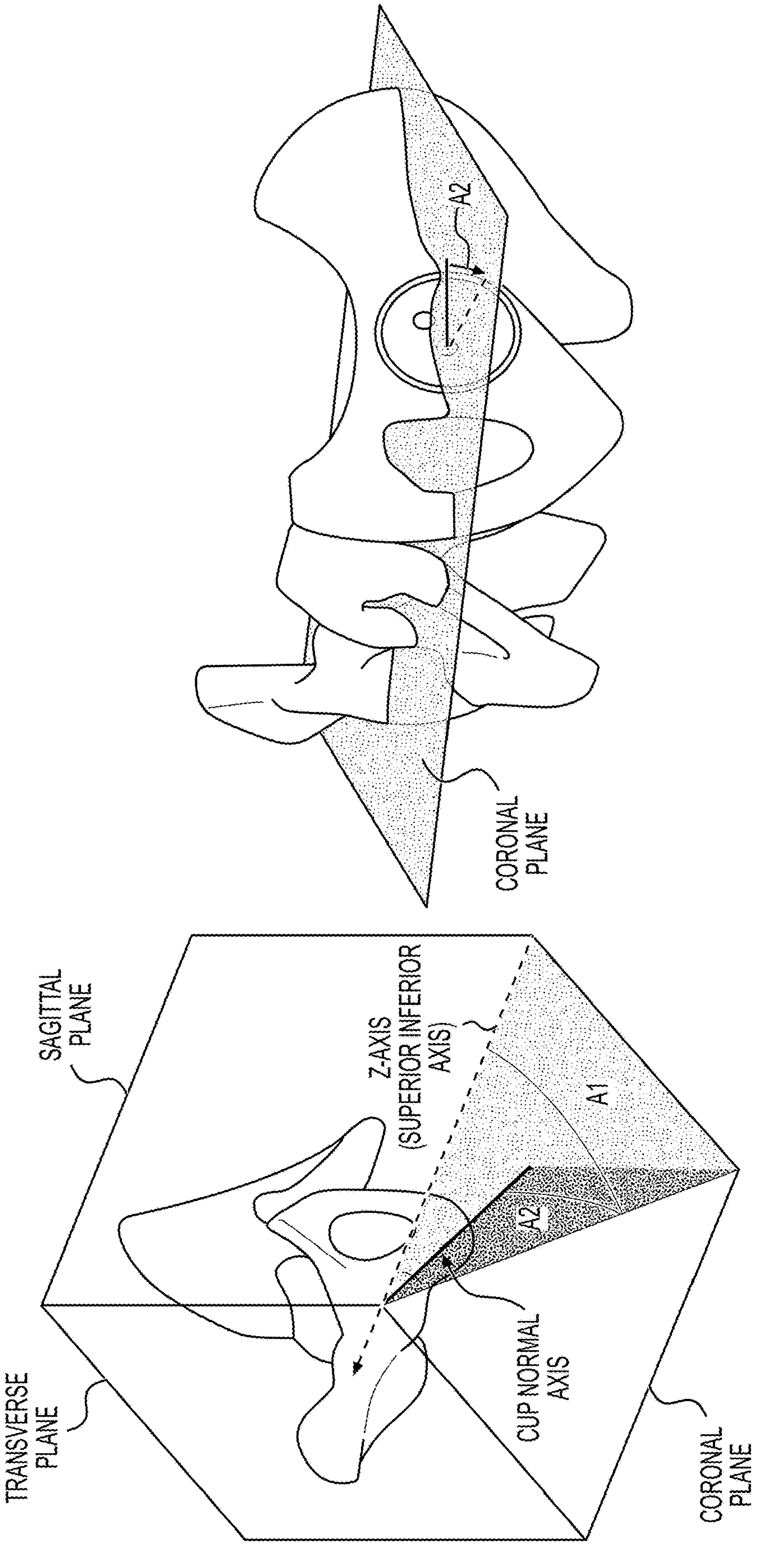
FIG. 10B illustrates a radiographic version angle measured relative to the coronal plane of the patient, in accordance with some embodiments of the present disclosure.

FIG. 10A illustrates a radiographic inclination angle measured in the coronal plane of the patient, in accordance with some embodiments of the present disclosure. In some embodiments, the surgeon may use a navigated instrument to palpate or paint the surface of the acetabular cavity of the patient to determine a center of rotation of the acetabulum, e.g., as discussed in more detail below. FIG. 10B illustrates a radiographic version angle measured relative to the coronal plane of the patient, in accordance with some embodiments of the present disclosure. The two pelvic reference planes (or coronal or frontal planes), the APP and FPP, are determined or defined using different landmarks and axes as shown on FIG. 11 and described in further detail below.

It is to be understood herein that although the user interfaces and associated operations are described as being performed in a certain sequence, they may be performed in other sequences while still being within disclosed embodiments (all the embodiments disclosed in the present disclosure). Moreover, it is not necessary that all of the user interfaces and/or described operations be performed. Instead, fewer operations may be performed while still being within disclosed embodiments.

Figure 11:
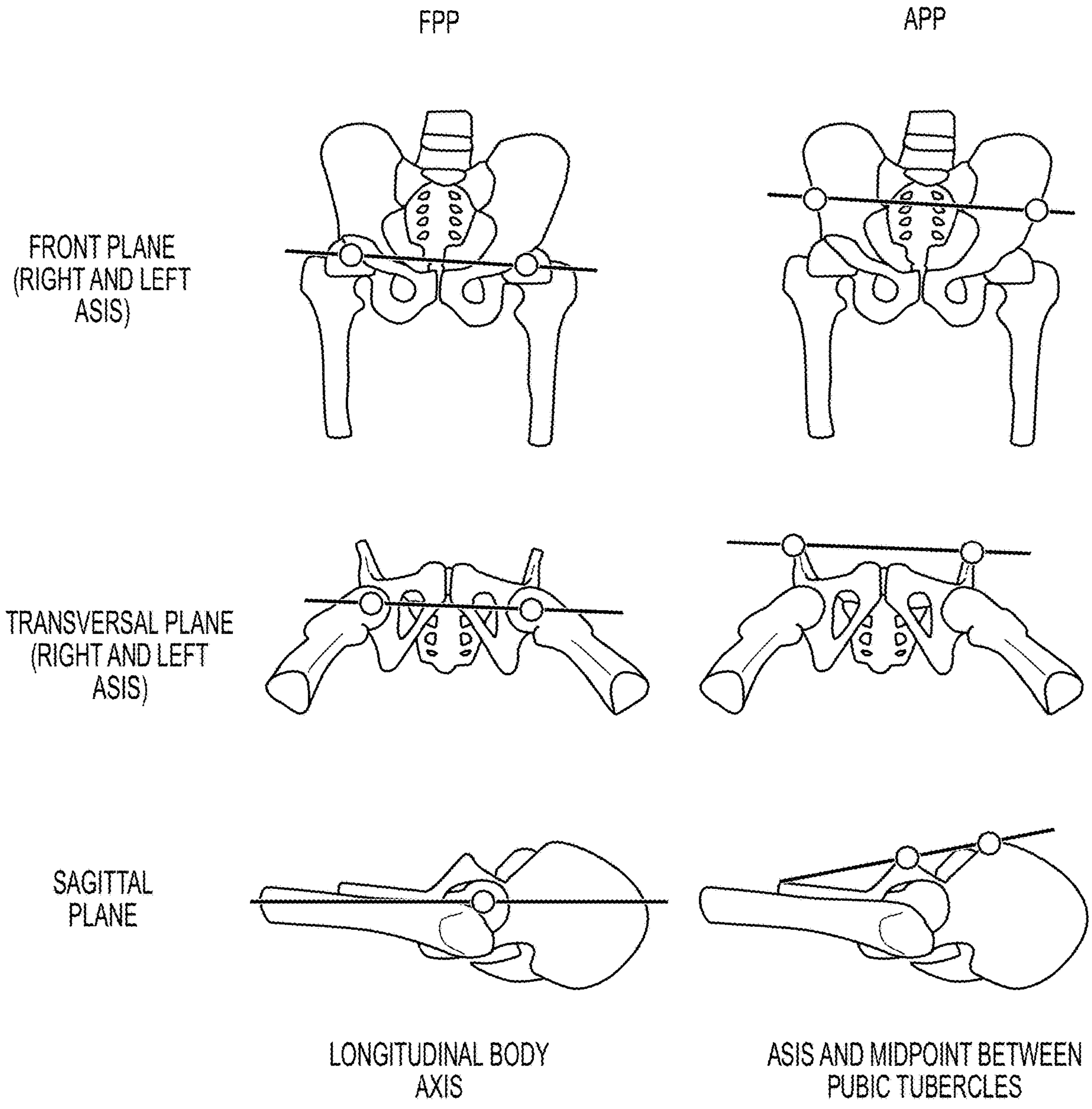
FIG. 11 illustrates different views of landmarks and axes for registration of a functional pelvic plane (FPP) and an anterior pelvic plane (APP) of a patient, in accordance with some embodiments of the present disclosure.

During a patient registration procedure, landmarks used to register patient anatomy can be extracted using either single point palpation collection or surface painting (resulting in a point cloud of locations). FIG. 11 illustrates different views of landmarks and axes for registration of a functional pelvic plane (FPP) and an anterior pelvic plane (APP) of a patient, in accordance with some embodiments of the present disclosure. The landmarks and axes used to register the APP and FPP planes are described in more detail in U.S. patent application Ser. No. 18/430,077, previously incorporated by reference herein.

Further, U.S. patent application Ser. No. 18/430,077 discloses processes for registration of a pelvic acetabulum of a patient (including painting the acetabular cavity), in accordance with various embodiments of the present disclosure. For example, to define the APP and FPP origins, the pelvic acetabular center of rotation can be determined after removing the femoral head of the patient from the acetabular cavity. The acetabular cavity may be made accessible by cutting the femoral neck and by removing the femoral head from the acetabular cavity. In some embodiments, a cork screw instrument may be used to remove the femoral head from the acetabular cavity. The surface of the acetabular cavity can then be painted using the navigated instrument (e.g., the stylus) as described herein. For example, the surgeon may use the navigated instrument (e.g., stylus 500) to palpate the surface of the acetabular cavity, as the tracking camera measures the position of the ball 610 on the end of the stylus 500 in a continuous way. This process provides a cloud of points for the measured positions (locations). At the same time, the tracking camera may also monitor and track the pose of the patient DRB 116 attached to the pelvis such that the pose of the stylus 500 can be tracked relative to the pose of the patient DRB 116. Alternatively, the surgeon may subsequently measure a predefined number or percentage of points by palpating them one-by-one. Based on these points and the tracking data of the stylus 500 and patient DRB 116, the center of rotation of the pelvic acetabular cavity is determined. Additionally, based on these points, the surface of the acetabular cavity may be registered in the system and/or a 3D model may be generated or modified based on these points.

Next, the acetabular cavity shape can be recreated (e.g., in a 3D model) by the system based on the measured cloud of points and using other algorithms, e.g., for outlier removals and surface fitting.

While certain imageless approaches are described herein and in U.S. patent application Ser. No. 18/430,077, previously incorporated by reference herein, there may be at least two different example methods of imagelessly registering the pelvis to the tracking coordinate of the tracking system (e.g., optical coordinate system). In both example methods, with continuing reference to FIGS. 1-7, 10 and 11, a center of rotation of the acetabulum is determined, for example, based on palpation either by touching multiple points on the inside of the acetabulum with a navigated instrument/probe (e.g., ball tip 610 of stylus 500, FIG. 5) or by continuously surface painting without lifting the navigated instrument/probe. In a first method, an FPP is derived by a physician lining up a plane or axis defined by the navigated instrument along or parallel to the FPP. Once the center of rotation and FPP are determined, the system (either a navigation system or a combined navigation and robot system 100) has sufficient information to register the acetabulum in the coordinate system (e.g., optical coordinate system) of the camera tracking system 200. Registration may allow a navigation system or robotic system to track any navigated instrument or end effector or any tool attached to the end effector relative to the pelvis as tracked by a patient dynamic reference base 116 attached to the pelvis.

In a second example embodiment, an APP is derived by either touching various known points (e.g., left and right anterior superior iliac spine (ASIS) and pubic symphysis) with a navigated instrument, or by a physician lining up a plane or axis defined by the navigated instrument along or parallel to the APP. With the center of rotation and APP determined, the system (either a navigation system or a combined navigation and robot system 100) has sufficient information to register the acetabulum in the coordinate system (e.g., optical coordinate system) of the camera tracking system 200.

In both of the above-noted example methods, the tracking system may be constantly monitoring and tracking the pose of the patient DRB 116 attached to the pelvis while also tracking the navigated instrument (e.g., stylus 500) such that the pose of the instrument can be tracked relative to the pose of the patient DRB, at least for purposes of registering the pelvis relative to the patient DRB 116 in the tracking coordinate system of the camera tracking system 200.

Additional registration approaches described herein can include image-based and imageless workflows. Combinations of these registration approaches are also possible in keeping with the various disclosed embodiments.

Registration Approaches Using Pre-Operative CT

Pre-Operative CT and Intra-Operative Fluoroscopy

Figure 16:
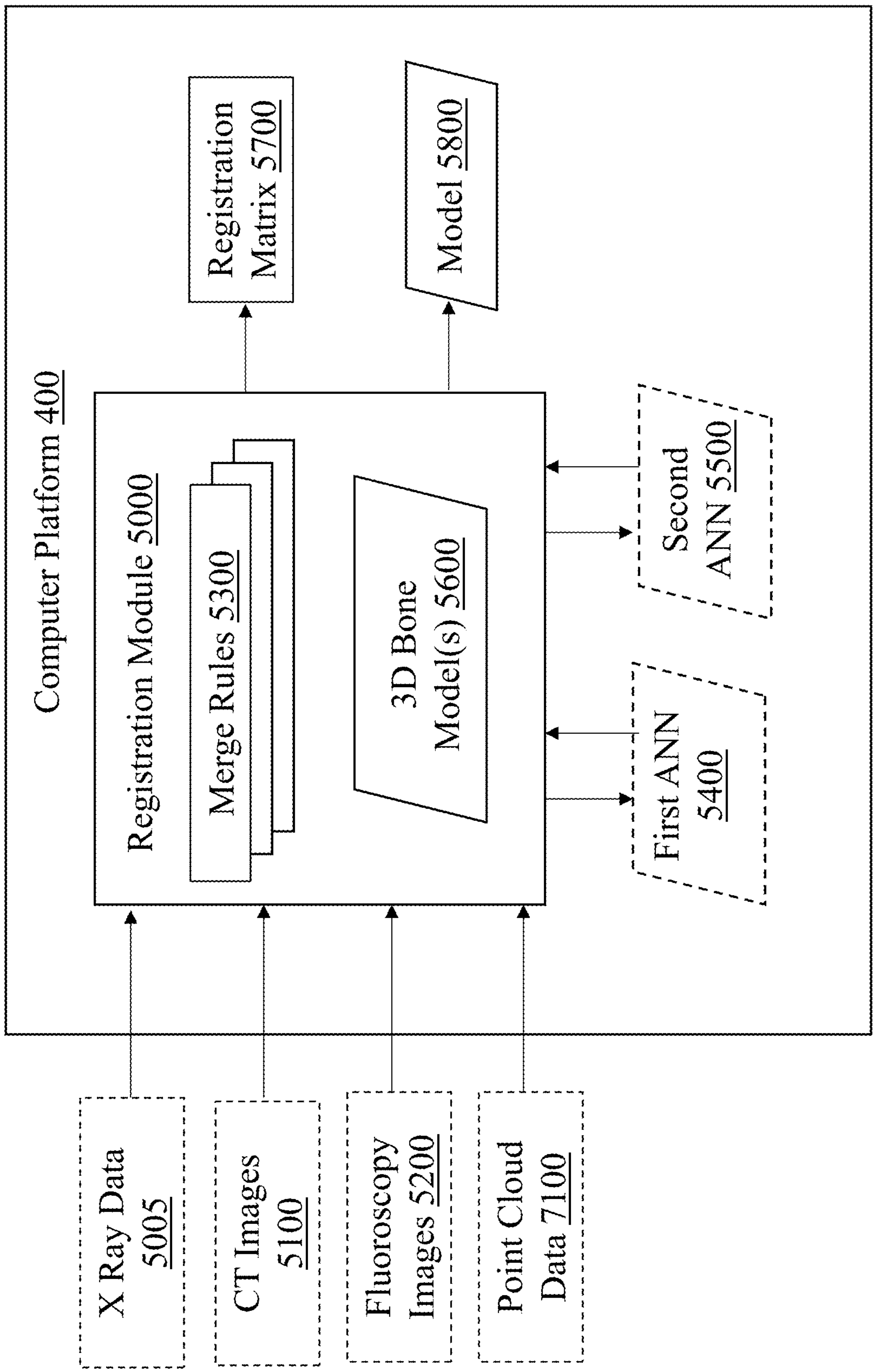
FIG. 16 is a data flow diagram illustrating functions of a computer platform, in accordance with various embodiments of the present disclosure.

FIGS. 12-17 illustrate processes in an example approach for registering a patient with a pre-op CT image and intra-op fluoro shots using the system shown in FIGS. 1-4. In various implementations, processes described relative to the registration approaches are performed by or otherwise controlled by the computer platform 400, e.g., via one or more programmable processors. In particular cases, the processes described relative to FIG. 12 relate to a surgery including a THA surgery. A data flow diagram relating to the registration processes illustrated in FIGS. 12-15 is shown in FIG. 16. As shown in FIG. 16, and with continuing reference to FIG. 12, the computer platform 400 includes a registration module 5000 that is configured to perform the following processes in registering a patient:

Process P4000 includes obtaining from an imaging device one or more computed tomography (CT) image(s) 5100 of a pelvic region of a patient captured prior to the surgery, e.g., pre-op from image data captured in the hours, days or weeks leading up to a surgery.

As is well known, raw x-ray images from the CT scanner are automatically converted to a 3D CT image/stack/volume which consists of a series of planar slices of the patient anatomy at various depth. The term CT image, CT volume, CT stack, 3D CT image, 3D image and 3D stack are all used herein interchangeably and refer to the same 3D image volume of a series of planar slices of the patient anatomy. In one embodiment, the raw x-ray images from a 360 degree CT scan are converted into 512 slices of the 3D volume.

In various embodiments, the 3D CT image 5100 of the pelvic region includes a target surgical area and a non-target surgical area. In a THA procedure, the target surgical area can include the acetabulum in the pelvis. An example of a non-target surgical area can include at least a portion of the patient's femur. In certain embodiments, the CT image(s) 5100 are captured while the patient is in the supine position, e.g., lying on his/her back.

From the CT images, the image processing software segments each planar slice of the 3D CT stack by identifying regions of interest (e.g., femur, acetabulum, sacrum and the like). The software then separates various parts such as the pelvis, femur and sacrum as three separate 3D stacks (three separate patient specific 3D bone model). All image processing may be done with the help of a trained neural network (machine learning algorithm) to identify the volume of each bone with respect to the image background such as femurs (left/right), pelvis, sacrum, and coccyx. The neural network has been trained with thousands or more of images of different patients which have been manually segmented. The neural network learns from the segmented images of other patients so that it can identify and segment various bones of a specific patient by processing the patient image (e.g., CT image) through the trained model. Each identified volume is used to generate an individual 3D bone model from it.

Since all of the bones have been segmented, it is a relatively easy process for the software to remove, for example, a segmented femur from the CT image volume while leaving the segmented pelvis in place to produce a patient specific 3D bone model that contains the pelvis without any other bone parts such as a femur. Other segmented bone parts such as a segmented spine portion can also be removed from the CT image volume with a similar process. This feature of removing bones (segmented or otherwise) such as removing femur from the pelvis is an important step as the later comparison steps may have fluoro shots whose femurs are not aligned in the same way as the original pre-op CT image.

In various implementations, additional inputs such as images and/or imaging data can be provided to the registration module 5000 to aid in registering the patient. For example, X-ray data 5005 can also be provided from preoperative X-rays captured, e.g., in the weeks, days, or hours leading up to the surgery. Certain combinations of inputs are described herein relative to FIG. 16, and it is understood that various combinations of inputs can aid in registering a patient according to various implementations.

Figure 12:
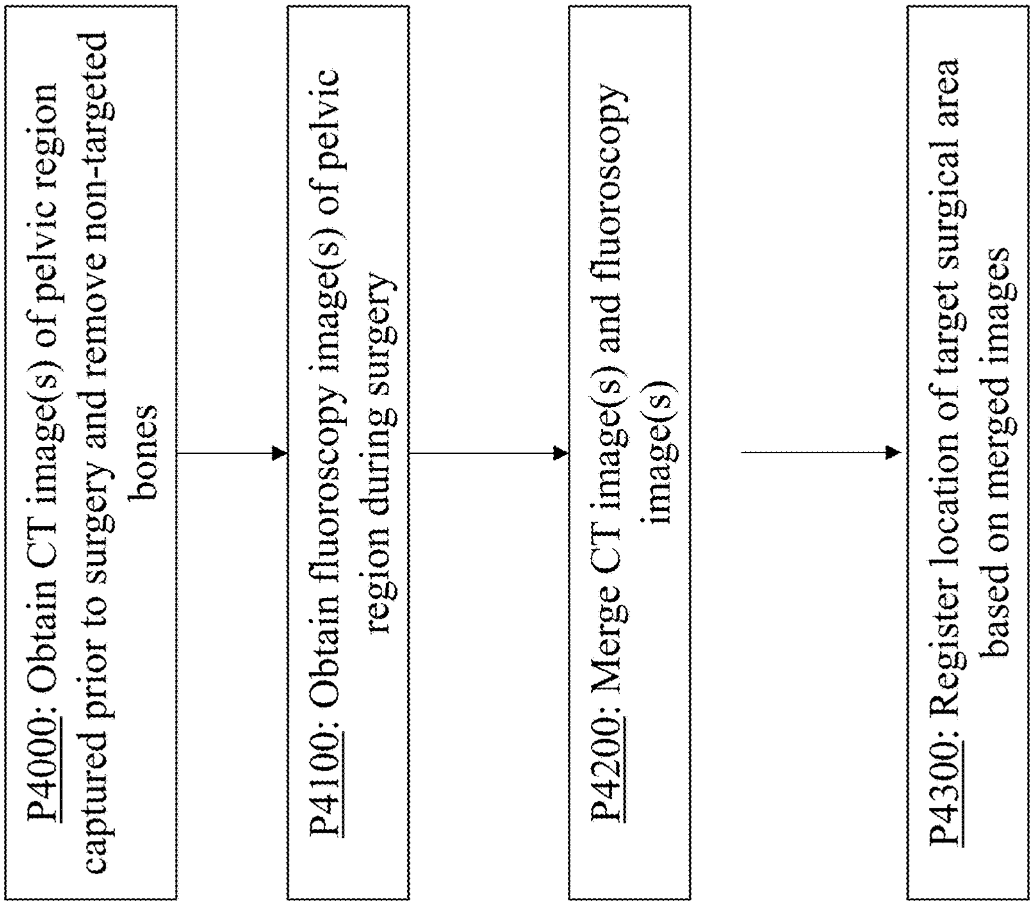
FIG. 12 illustrates a flowchart for registration of a target surgical area of a patient, in accordance with some embodiments of the present disclosure.

With continued reference to FIG. 12, process P4100 includes obtaining at least one fluoroscopy image 5200 of the pelvic region of the patient captured during the surgery while the cameras are tracking the optical markers on the registration fixture or on the C-arm of an imaging device to record the orientation at which the shots are being made. In one embodiment, one A-P fluoro shot and one lateral fluoro shot are captured. In another embodiment, two oblique fluoro shots that are orthogonal to each other may be captured. For example, one shot can be at 30 to 60 degrees to the axis perpendicular to the operating room table, and the other shot can be at −30 to −60 degrees to the same axis. These oblique shots may be preferable to AP and lateral shots because the lateral shot can be difficult to process due to inclusion of both femurs and both sides of the pelvis in the image.

These intra-op fluoro shots are taken with the help of a patient DRB 6200A attached to the pelvis and optionally 7000 (see FIG. 23), stereo navigation camera 200, computer station, fluoro imaging device (e.g., x-ray imaging device) and tracked fluoro fixture such that the computer station stores for each image taken all of the associated information including the radiopaque fiducials and the optical marker array of the registration fixture tracked by the camera at the time of capture, and DRB 6200A tracked by the camera at the time of capture. These information are used by the computer station for registration purposes for all of the embodiments disclosed herein.

Figure 13:
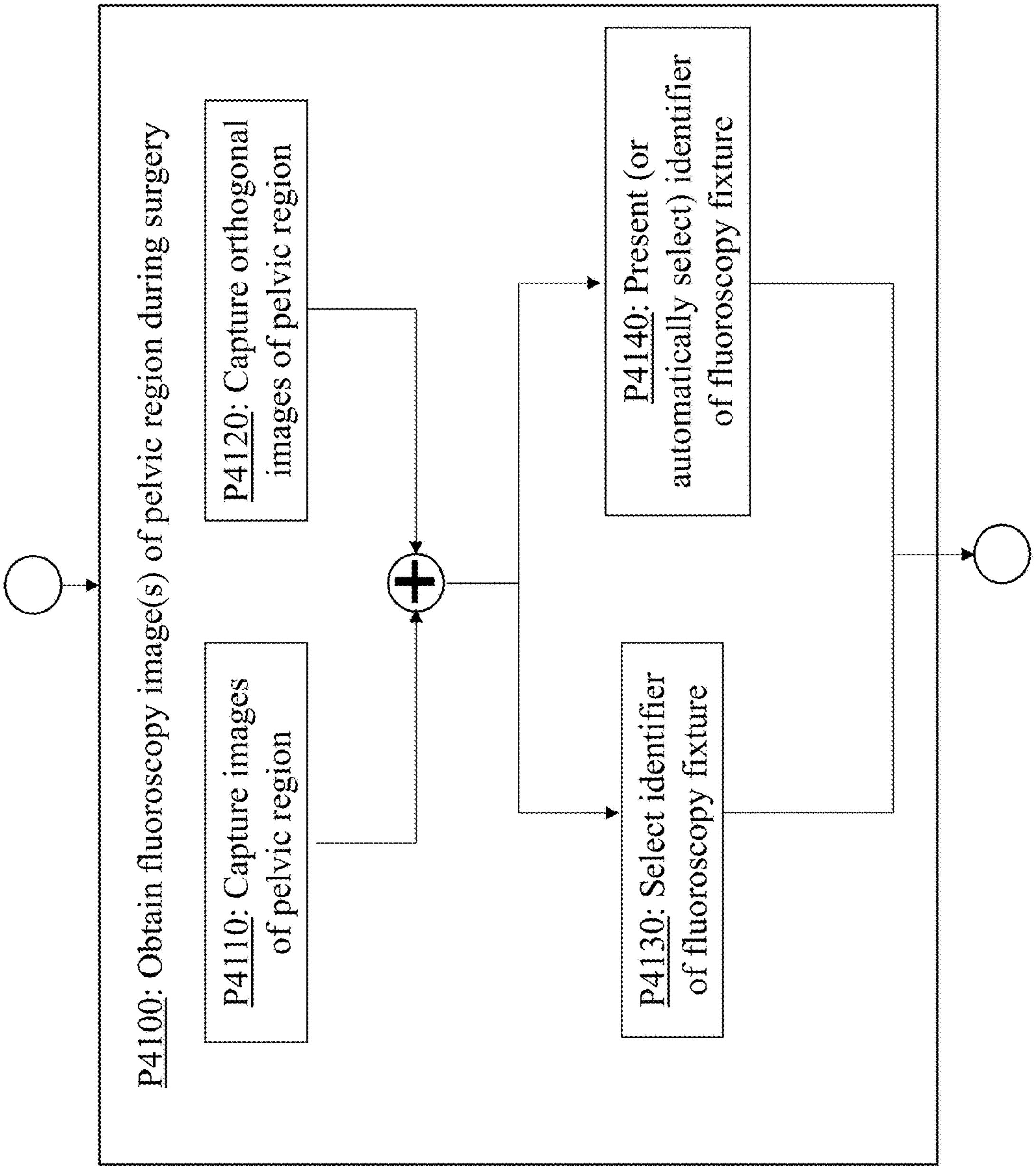
FIG. 13 shows sub-processes in the flowchart of FIG. 12, in accordance with some embodiments of the present disclosure.
Figure 14:
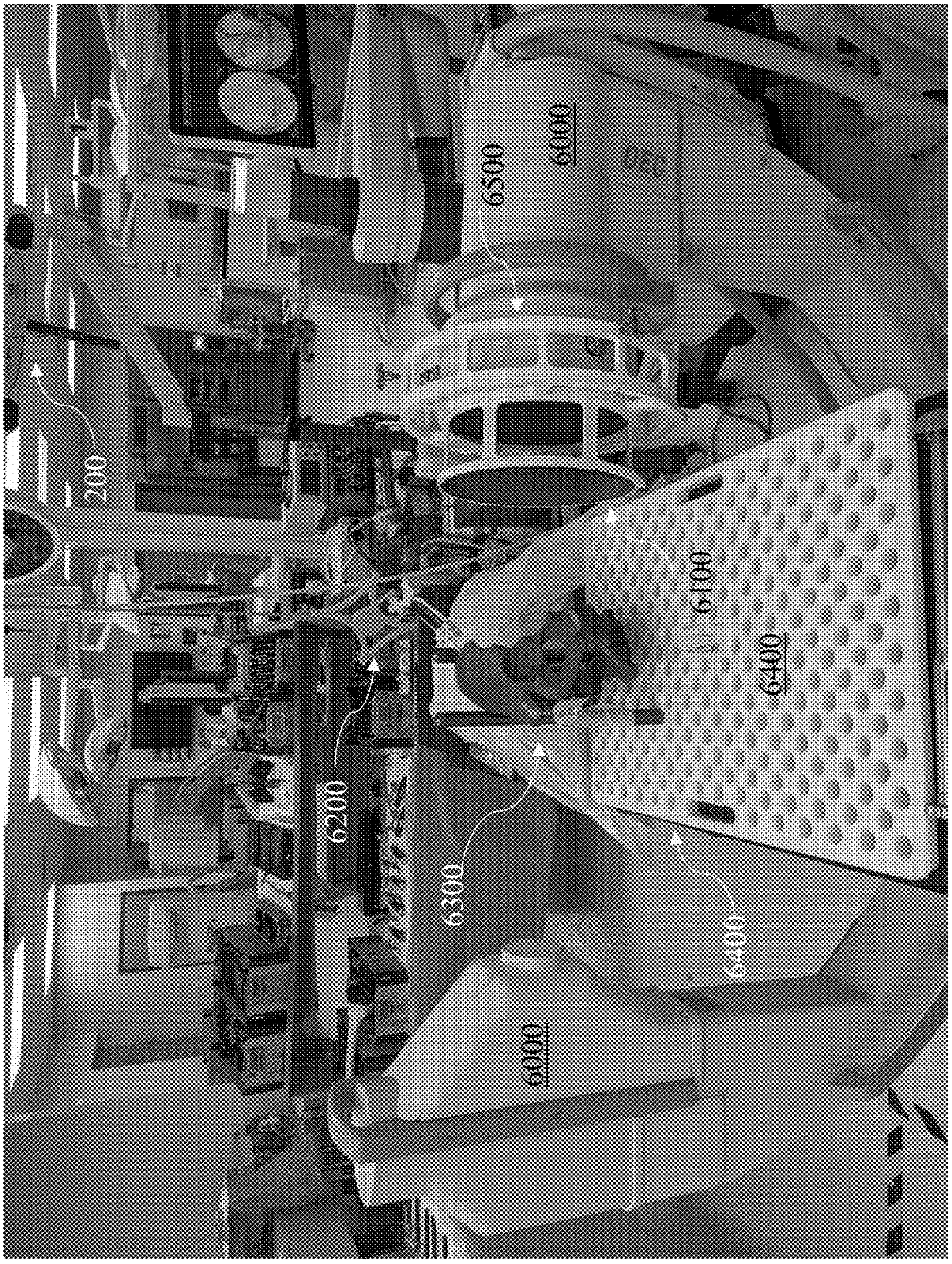
FIG. 14 illustrates an example operating space in accordance with some embodiments of the present disclosure.
Figure 15:
FIG. 15 illustrates fluoroscopy imaging gathered in an example operating space, in accordance with some embodiments of the present disclosure.

In this process, the fluoroscopy image 5200 is captured while the patient is in the surgical space, e.g., on the surgical table. FIG. 13 illustrates sub-processes in obtaining the fluoroscopy image of the pelvic region, which can include process P4110: taking oblique images (or "shots") of the pelvic region, and/or P4120: taking orthogonal images (or shots) of the pelvic region. These processes can be optionally combined, or performed in isolation. In one example, both oblique images of the pelvic region are taken and combined in one or more data files including fluoroscopy images. In a specific example, at least two fluoroscopy images are used to localize the patient. FIG. 14 shows an example operating space including a fluoroscopy machine 6000 with a fluoroscopy fixture 6100, along with a patient tracker 6200 (e.g., similar to DRB 116 in FIGS. 1-3 and/or reference element 602 in FIG. 5) attached to a model of a pelvis 6300 on an operating table 6400. Camera tracking system 200 is also depicted in FIG. 14. In this example, the model of pelvis 6300 represents a patient's pelvis when located on the operating table 6400. In this example, the fluoroscopy machine 6000 is positioned to capture AP images while the patient tracker 6200 (or, reference element) is attached to the pelvis 6300.

In particular implementations, distinct fluoroscopy fixtures 6100 are available to capture distinct fluoroscopy images. For example, two or more fluoroscopy fixtures may be available in some cases, and in additional cases, up to three distinct fluoroscopy fixtures may be available. In a particular example, a 9 inch fixture or a 12 inch fixture can be configured to connect (e.g., clamp) to a circular image intensifier 6500 of the fixture 6100, which in some cases, has a similar diameter. In some embodiments, an additional flat panel option is available for use with flat panel style C-arm. In certain examples, the 9 inch and 12 inch fixtures are each factory calibrated, and the flat panel includes a calibration file, e.g., on a data file, which can be selected by the user during surgery. As noted herein, when using the flat panel the data file can be loaded onto the system and subsequently selected for each case. These processes are illustrated with continuing reference to FIG. 13. In optional sub-process P4130, the identifier (e.g., type and serial number) of the fluoroscopy fixture 6100 (e.g., imaging device) is selected, e.g., by the surgeon and/or assistant using an interface, e.g., a graphical user interface, touch screen interface, or other visual and/or interactive interface on a display, e.g., on display 110 (FIGS. 1-3). In optional processes, a data connector for the fluoroscopy fixture is inserted into the computer platform 400 (e.g., via a data connector such as a USB port) in process P4140, and the identifier (e.g., type and serial number) of the fluoroscopy fixture is either automatically selected or presented on the interface of computer platform 400 for selection, e.g., by the surgeon and/or assistant using the display (e.g., interface) 110.

As noted herein, in various implementations at least two fluoroscopy images 5200 are used to localize the patient, e.g., the pelvis 6300. With reference to the two-dimensional (2D) fluoroscopy image 6600 shown on interface 110 in FIG. 15, radiopaque tracking markers 6700 are used to localize the pelvis 6300 in 2D space. In certain cases, these markers 6700 can be transformed, or otherwise correlated with known locations of the patient tracker 6200 (including fiducials) to locate portions of the pelvis 6300 in 2D space.

Returning to FIG. 12, in various embodiments, following obtaining the CT image(s) 5100 and fluoroscopy image(s) 5200, the computer platform 400 (e.g., via registration module 5000) is further configured to:

At process P4200: merge the CT image(s) 5100 and fluoroscopy image(s) 5200.

As noted herein, in various embodiments the CT image(s) 5100 and fluoroscopy image(s) 5200 can both include target surgical areas (e.g., pelvis) and non-target surgical areas (e.g., portions of the femur). As such, the registration module 5000 is configured in various embodiments to apply the merge rules 5300 to identify obstructing, or other non-target areas in the anatomy from the CT image(s) 5100 and fluoroscopy image(s) 5200, e.g., via image-to-image mapping. As is also noted herein, in various embodiments two or more fluoroscopy images 5200 are captured intra-operatively to aid in registering the patient. For example, two or more fluoroscopy images 5200 can be captured of the hip, including the pelvis, with the femur being partially visible in the image(s). In certain examples, two or more images 5200 are taken from distinct orientations, including two or more of antero-posterior, lateral, oblique, etc. In some examples, the surgeon or assistant captures the fluoroscopy images 5200 of the patient, using the camera tracking system 200, the fluoroscopy machine 6000 with fluoroscopy fixture 6100, along with the patient tracker 6200 (FIG. 14).

With reference to step P4200, there may be two ways of merging. In one way, a CT image/volume with the femur removed (preferably only the pelvis is present in the image) is compared against the fluoro shots that contains the pelvis and femur. The comparison is for example an iterative process of generating a DRR (digitally reconstructed radiograph or simulated fluoro shot) at a particular angle and projecting it to the fluoro shot to see if there is an image match and if not generating a different DRR at a slightly different angle until the best match is found. In another way, prior to any comparison, an image processing software removes all bones including femur from the fluoro shots as well as from the CT image. In this way, a closer match may be found between the DRR of the CT volume and the fluoro shot.

Figure 17:
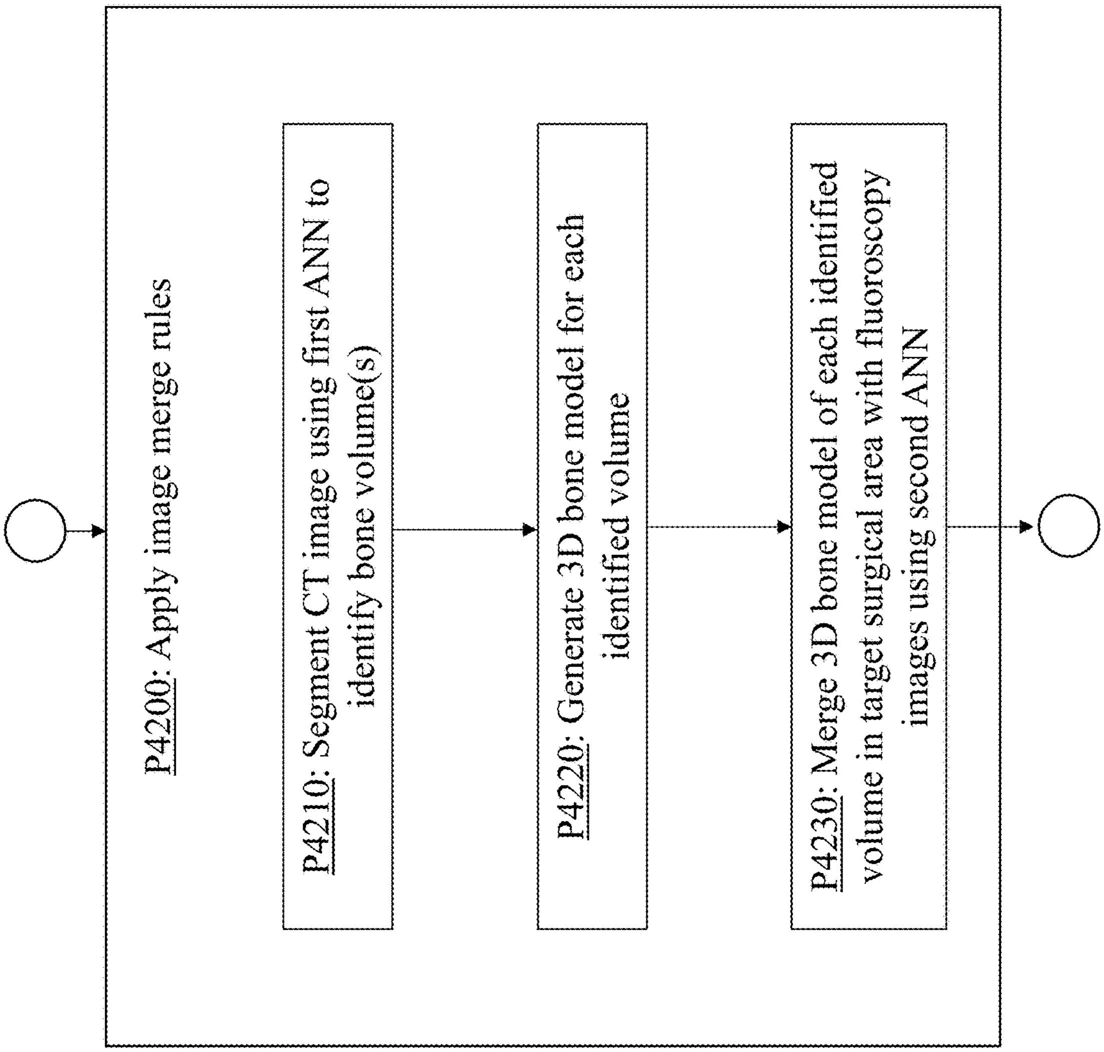
FIG. 17 illustrates sub-processes in the flowchart of FIG. 12, in accordance with some embodiments of the present disclosure.

FIG. 16 shows the registration module 5000 in communication with at least one artificial neural network (ANN), e.g., a first ANN 5400 and a second ANN 5500 to aid in applying merge rules 5300 according to various embodiments. ANNs 5400, 5500 are illustrated in phantom as optional in certain implementations. It is understood that ANNs 5400 and 5500 can include one or more machine learning (ML) algorithms that can be configured (e.g., trained) to perform processes in identifying characteristics of images and/or patient anatomy. In various implementations, one or both ANNs is trained using training data to aid in identifying characteristics of images and/or patient anatomy. In some cases, at least a portion of one or more ANNs is stored locally at the computer platform 400. In further cases, at least a portion of one or more ANN is run remotely, e.g., in a network connected processor, and is periodically updated locally at the computer platform 400. FIG. 17 includes a flow diagram illustrating processes in applying the merge rules 5300 to CT image(s) 5100 and fluoroscopy image(s) 5200, including:

At process P4210 (performed either pre-surgically or intra-operatively): segmenting the CT image 5100 using a first artificial neural network (ANN) 5400 to identify a volume of a plurality of bones in the CT image 5100. In various implementations, the first ANN 5400 includes a trained ML algorithm. In some examples, the ML algorithm in the first ANN 5400 is trained by providing a known CT image dataset with annotated portions of images representing target surgical areas (e.g., the pelvis region) and non-target surgical areas (e.g., the femur or portions thereof). In some cases, the images are annotated manually, e.g., via user input to a computer editing and/or drawing software and/or via annotations to physical copies of images. In these embodiments, the trained first ANN 5400 can be configured (e.g., trained and/or otherwise programmed) to identify which bone shape corresponds to a pelvis, a femur or something else on the CT image 5100. In particular embodiments, each of the bones in the CT image 5100 is identified as a volume with respect to the background. For example, in the context of a THA procedure, identifying a volume of one or more bones can include identifying one or both femurs (L/R), the pelvis, the sacrum, and the coccyx.

Process P4220: includes generating a three-dimensional (3D) bone model 5600 for each identified volume. In various implementations, multiple CT images 5100 are used to generate the 3D bone model 5600 for each volume, e.g., bone, such as the femurs (L/R), the pelvis, the sacrum, and the coccyx. In particular cases, the 3D bone model(s) 5600 are generated based on user-selected locations in CT images 5100. For example, a user can select points (or locations) in CT images 5100 to define parameters for the 3D bone model(s) 5600. In other cases, or in additional cases, the ANN 5400 can aid in selecting points from the CT images 5100 to define parameters for the 3D bone model(s) 5600. In one example, the 3D bone model(s) 5600 can include one or more digitally reconstructed radiographs created from the CT images 5100.

Process P4230: includes merging the 3D bone model 5600 of each identified volume in the target surgical area with the fluoroscopy images 5200 of the pelvic region using the second artificial neural network (ANN) 5500. In various implementations, the second ANN 5500 includes a trained ML algorithm. In some examples, the ML algorithm in the second ANN 5500 is trained by providing a known fluoroscopy image dataset with annotated portions of images representing target surgical areas (e.g., the pelvis region) and non-target surgical areas (e.g., the femur or portions thereof). In some cases, the images are annotated manually, e.g., via user input to computer editing and/or drawing software and/or via annotations to physical copies of images. In these embodiments, the trained second ANN 5500 can be configured (e.g., trained and/or otherwise programmed) to identify which bone shape corresponds to a pelvis, a femur or something else on the fluoroscopy image 5200. In particular embodiments, each surface of the bones in the fluoroscopy image 5200 is identified as a contour with respect to the background and other bones. For example, in the context of a THA procedure, identifying a contour of one or more bones can include identifying a surface/contour of one or both femurs (L/R), the pelvis, the sacrum, and the coccyx.

In particular implementations, merging the 3D bone model 5600 of each identified volume in the target surgical area with the fluoroscopy images 5200 of the pelvic region using the second artificial neural network (ANN) 5500 (P7200) or an image processing software without any neural network includes sub-processes, including: i) generating each 3D bone model 5600 which excludes non-targeted area for identified volumes in the non-target area, ii) identifying geometrical similarities between each generated 3D bone model 5600 for identified volumes in the target area and the fluoroscopy images 5200 (which may or may not contain non-targeted bones), iii) for a given orientation of the fluoroscopy images 5200, applying a best geometrical match rule for a given orientation of the 3D bone model 5600 for identified volumes in the target surgical area, and iv) registering the location of the target surgical area based on the applied best geometrical match rule based on the tracked data including pose of the DRB from the cameras, reference arrays in the registration fixture at the time of taking the fluoro shots from the cameras and radiopaque markers of the registration fixture contained in the fluoro shots. In various implementations, processes of merging the CT images 5100 and fluoroscopy images 5200 does not necessarily include removing or otherwise isolating non-target surgical areas from the fluoroscopy images 5200. That is, the processes of removing the 3D bone models 5600 for identified non-target areas (i) and identifying the geometrical similarities (ii) can effectively isolate the process of applying a best geometrical match rule (iii) to target surgical areas without requiring separate processing of the fluoroscopy images 5200 to remove non-target areas.

In particular cases, as noted herein, the registered location of the target surgical area is saved in a final registration matrix, which can be displayed during surgery, e.g., at an interface on display 110.

In certain cases, removing each 3D bone model 5600 for identified volumes in the non-target area includes segmenting a CT volume and separating the segmented CT volume into multiple models (e.g., computer aided design, or CAD models) of the bone to individually display, remove, and/or process the non-target areas. This approach is described in greater detail in U.S. patent application Ser. No. 17/088,853, filed on Nov. 4, 2020, entitled "SYSTEM AND METHOD OF DETERMINING OPTIMAL 3-DIMENSIONAL POSITION AND ORIENTATION OF IMAGING DEVICE FOR IMAGING PATIENT BONES"), which is entirely incorporated by reference herein.

Returning to FIG. 12, in various embodiments, after merging the CT image(s) 5100 and fluoroscopy image(s) 5200, the registration module 5000 performs:

In process P4300, based on the merged CT image(s) 5100 and fluoroscopy image(s) 5200, the registration module 5000 registers a location of the target surgical area based on the radiopaque fiducials contained in the fluoroscopy image and the pose of the optical marker array of the registration fixture at the time of capture, and pose of the optical markers of the DRB 6200A at the time of capture. In a particular implementation, the registration module 5000 generates a final registration matrix 5700 (FIG. 16) of the target surgical area, e.g., the pelvis region such as pelvis 6300 shown in FIG. 14. In particular cases, the registration matrix 5700 is displayed on the interface 110, e.g., as an overlay on an image of the patient, as a separate image or model, or in any other format that conveys to the surgeon and/or assistant the location of the target surgical area. In a particular embodiment, the registration module 5000 generates a model 5800 of the target surgical area based on the registered location (FIG. 16). The model 5800 can include one or more data files, and can be displayed (e.g., via interface 110) to enhance the efficiency and/or effectiveness of the surgical procedure.

Pre-Operative CT and Intra-Operative Point Cloud

In various additional implementations, pre-operative CT imaging is combined with an intra-operative point cloud (gathered by a navigated instrument such as ball tip stylus 500 (FIGS. 5-7) to effectively register a surgical patient. In these cases, a system such as the computer platform 400 can be configured to register a surgical patient using pre-operative CT images and the intra-operative point cloud gathered by the stylus 500. In various embodiments, the registration module 5000 (FIG. 16) includes a set of merge rules 5300 for merging CT images 5100 with point cloud data 7100. In some examples, the registration module 5000 is configured to communicate with the first ANN 5400 as discussed relative to embodiments depicted in FIGS. 12-15. In some optional examples, the registration module 5000 is further configured to communicate with a second ANN 5500 that is configured to aid with aligning sections of the point cloud with segmented or non-segmented CT images 5100. In some cases, the second ANN 5500 includes a trained machine learning algorithm that is trained by providing an overlayed point cloud dataset with a CT image dataset including annotated target areas and non-target areas. As discussed relative to FIG. 16, in some cases, the first ANN 5400 and/or second ANN 5500 can be located (e.g., stored or otherwise executed) at the computer platform 400 and/or located remotely and accessed via a network or cloud connection.

Figure 18:
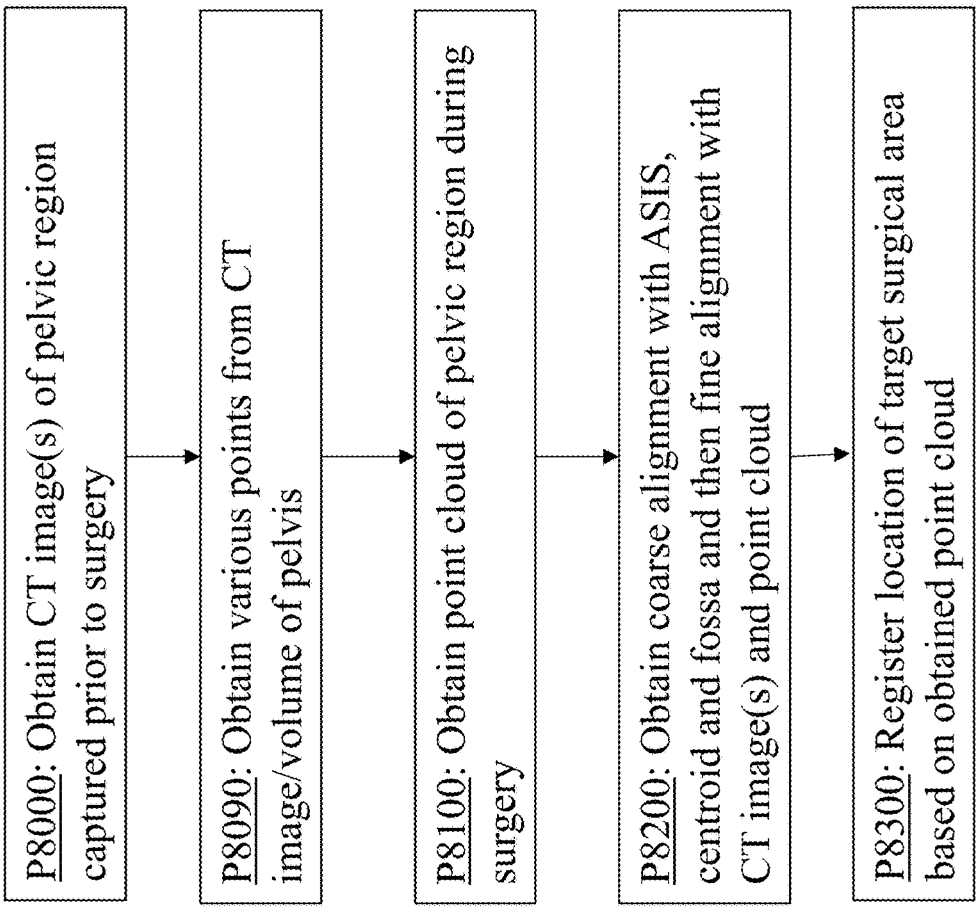
FIG. 18 illustrates a flowchart for registration of a target surgical area of a patient, in accordance with additional embodiments of the present disclosure.

FIG. 18 shows example processes performed by a registration module 5000 (FIG. 16) in a method which uses a pre-op CT image and intra-op point cloud collection according to various implementations. The registration is done is preferably done with a coarse alignment using various points on the CT image and then a fine alignment using the point cloud, the processes including:

Process P8000, which includes obtaining a pre-op computed tomography (CT) image 5100 of a pelvic region of a patient captured prior to the surgery, the CT image 5100 of the pelvic region including a target surgical area and a non-target surgical area. In certain cases, process P8000 can include overlap with process P4000, described with respect to FIG. 12.

In P8000, the CT image is segmented with image processing to identify various bone parts. As in other image processing, the software generates three separate 3D CT volume/model from the 3D CT image: 3D pelvis, 3D femur and 3D sacrum. For purposes of registration, the registration module uses the 3D pelvis model which excludes all other non-targeted bones including femur. The segmented data for the 3D pelvis model may include an acetabulum edge, inner and outer surfaces of the acetabulum and a fossa. The segmentation and all other image processing can be performed by an image processing software such as the first ANN 5400.

Figure 19:
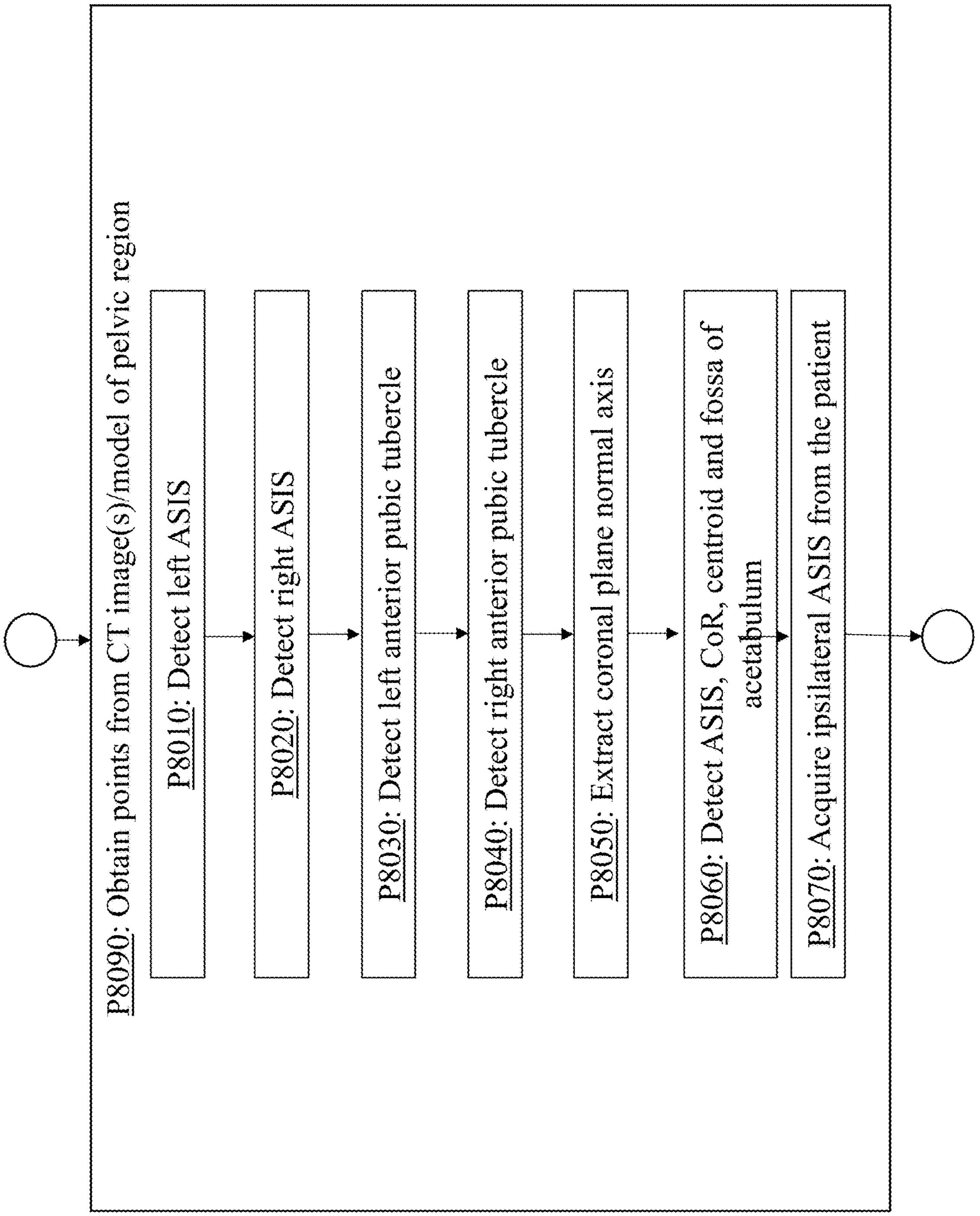
FIG. 19 illustrates sub-processes in the flowchart of FIG. 18, in accordance with some embodiments of the present disclosure.

In particular additional implementations, process P8090 may include defining the anterior pelvic plane (APP) and/or the functional pelvic plane (FPP), which can include various sub-processes. The APP and FPP can be constructed from various biomechanical landmarks detected in the CT image(s) 5100, including for example, the left/right anterior superior iliac spine (ASIS). FIG. 19 illustrates certain of these sub-processes, including for example:

- in process P8010, detecting the left ASIS from the CT image(s) 5100;
- in process P8020, detecting the right ASIS from CT image(s) 5100;
- in process P8030, detecting the left anterior pubic tubercle from CT image(s) 5100; and
- in process P8040, detecting the right anterior pubic tubercle from CT image(s) 5100.

In certain cases, processes P8010-P8040 can provide sufficient image data to define the APP.

Further processes can include process P8050, including extracting the coronal plane normal axis from the CT image(s) 5100. In certain aspects, processes P8010-P8050 can provide sufficient image data to define the FPP. The APP and FPP are generally used for purposes of planning a surgery, rather than for registration purposes although they can be used for the registration purposes and for registration verification purposes.

Following detection of the APP and FPP, in certain cases the acetabulum center of rotation (CoR) and centroid of the acetabulum can be detected (P8060) from the CT image/volume. The CoR of the acetabulum can be identified, e.g., using a best fit sphere in some cases which is derived from the CT image/volume. The centroid can be derived by detecting the edges of the acetabulum.

In process P8070, the user interface asks the user, through the user interface, to obtain from the patient an ipsilateral ASIS from the patient with the navigated instrument 500 tracked by the cameras and with the DRB 6200 attached to the patient. The actual ASIS may be hidden under a skin of the patient, but can be pointed to by the navigated instrument 500 over the skin for a close approximation of the point location.

In process P8100, the registration module 5000 through the user interface asks the user on the display device to point the navigated instrument 500 to collect various points on the pelvis to obtain a point cloud (point cloud data 7100) of the pelvic region of the patient during the surgery. The user is instructed to continuously palpate or "paint" in a smooth motion the inner surface and edges of the acetabulum, for example, in a zig zag fashion and point to the acetabulum fossa while the cameras are tracking the navigated instrument 500 and the DRB 6200 attached to the pelvis. The atraumatic tip 610 contacts the acetabulum surface but should not penetrate any portion of the bony surface or cartilage. During the point cloud collection, the registration software 5000 continuously tracks and stores through the cameras 204 the pose of the navigated instrument 500 through optical markers 604 as well as the pose of the DRB 6200 through optical markers. When a sufficient amount of point cloud data has been gathered, the software processes the points to fit a 3D sphere (which is geometrically similar to the acetabulum cavity). From the fitted 3D sphere, its center is considered to be equivalent to the center of rotation of the acetabulum of the patient.

The centroid is derived from the corona of points acquired on the acetabulum edges with the navigated instrument 500.

In process P8200, the registration module 5000 performs a coarse alignment of the CT image/volume to the patient pelvis to establish a starting point and then using the obtained starting point, perform a fine registration. While the registration may perform adequately without the coarse alignment, using the coarse alignment avoids the potential of the software to fall into a local minimum during the search for the optimization of alignment between the point cloud and the 3D bone model (i.e., CT image/volume). The coarse alignment also saves a substantial amount of image processing time in order to reduce the surgery time and improve patient outcome due to less time required for the surgery.

In the coarse alignment, one or more points as detected by the image processing software (ASIS, centroid, CoR, and fossa) are compared against the same points as obtained with the navigated instrument 500 on the patient. In one embodiment, ASIS and CoR are used for coarse alignment. In another embodiment, ASIS, CoR and fossa or ASIS, centroid and fossa are used. In yet another embodiment, ASIS and fossa are used. In another embodiment, all four points are used for coarse alignment. Generally, it is preferable to compare at least three points.

In some cases, the point cloud includes a plurality of data points 7100 detected on the pelvic region of the patient and captured by the navigated instrument (e.g., stylus 500). Due to the localized nature of the point cloud capture, in various implementations the point cloud excludes the non-target surgical area, e.g., portions of the femur. In particular cases, data points 7100 in the point cloud are acquired from at least one bony surface of the target surgical area, e.g., at least one bony surface such as: an edge of the acetabulum, an inner surface of the acetabulum, or a fossa surface of the acetabulum. In certain examples, the data points 7100 in the point cloud are acquired from all of: an edge of the acetabulum, an inner surface of the acetabulum, and a fossa of the acetabulum. According to some embodiments, other areas of the pelvic surface can be captured using the navigated instrument 500, and in certain cases, can be used to perform surface matching and/or precision checks as described herein. As described herein, e.g., relative to FIGS. 5-7, certain aspects of obtaining point cloud data 7100 include accessing the patient's surgical target, locating and recording a surveillance check point, measuring the patient's leg length and any applicable offset, and removing the femoral head to enable point cloud acquisition. These preliminary processes are described in detail in U.S. patent application Ser. No. 18/430,077 and U.S. patent application Ser. No. 17/088,853, each previously incorporated by reference herein.

Once coarse registration is completed, the registration software 5000 knows the starting point (e.g., particular orientation and angle of the CT model/stack). With the derived starting point, process P8200 performs a fine alignment of the CT image 5100 with the point cloud 7100 using a set of merge routine or rules. The merging/alignment matches the orientation and shape of the 3D image of the acetabulum from the point cloud to the acetabulum in the CT image. In one embodiment, the software attempts to match the segmented data from the CT image to the point cloud or the segmented data of the point cloud. In some of these cases, as discussed relative to FIGS. 13-16, segmenting the CT image 5100 and generating the 3D bone model 5600 can be performed pre-operatively or intra-operatively in various implementations.

In various embodiments, applying the set of merge rules 5300 further includes: comparing the acquisition of the at least one bony surface (e.g., point cloud data 7100) with a precision threshold. As noted herein, the point cloud data 7100 can include bony surface data about locations of one or more bony surfaces, including but not limited to: the acetabulum edge, the inner and outer surfaces of the acetabulum, and the fossa. In certain cases, the precision threshold is based on an acceptable statistical deviation, e.g., based on a level of deviation of one or more subsets of the point cloud data 7100 from a remainder of the point cloud data 7100. In further cases, the precision threshold is based on an acceptable deviation from the location of surfaces as indicated by the segmented CT image 5100 and/or the 3D bone model 5800. In some of these cases, the precision threshold includes a range or a subset of thresholds that vary based on the location of surfaces, characteristic of surfaces, etc.

According to particular cases, if the acquisition of the at least one bony surface (e.g., cloud point data 7100) fails to satisfy the precision threshold, the process includes repeating acquisition of the points in the point cloud (P8100). If the acquisition of the at least one bony surface (e.g., point cloud data 7100) satisfies the precision threshold, the process includes merging the point cloud 7100 with the 3D bone model 5800 in process P8200. In certain implementations, merging the point cloud 7100 with the 3D bone model 5800 includes aligning respective sections of the point cloud 7100 with corresponding 3D bone model 5800. In certain cases, referring to FIG. 16, aligning the sections of the point cloud 7100 with corresponding the 3D bone model 5800 can be performed using a second ANN 5500, including e.g., a trained machine learning algorithm that is trained by providing an overlayed point cloud dataset with a CT image dataset including annotated target areas and non-target areas. In other implementations, the merge rules 5300 need not necessarily use a second ANN 5500, for example, where merge rules 5300 define segmentation and alignment rules including correspondence between segmented CT images 5100 (and/or model 5800) and point cloud data 7100.

Returning to FIG. 18, if the merge rules (including precision check of point cloud data 7100) are satisfied, an additional process P8300 can include registering a location of the target surgical area (e.g., as matrix or transform vector 5700 and/or model 5800) based on the merged CT image(s) 5100 and point cloud 7100. Registration can be performed in a similar manner as described with reference to P4300 in FIG. 12. In a particular implementation, the registration module 5000 generates a final registration matrix 5700 of the target surgical area, e.g., the pelvis region based on the tracked data with respect to the optical markers in the DRB 6200 and the optical markers 604 of the tracked navigation instrument 500. In particular cases, the registration matrix 5700 is displayed on the interface 110, e.g., as an overlay on an image of the patient, as a separate image or model, or in any other format that conveys to the surgeon and/or assistant the location of the target surgical area (FIG. 16). In a particular embodiment, the registration module 5000 generates a model 5800 of the target surgical area based on the registered location. The model 5800 can include one or more data files, and can be displayed (e.g., via interface 110) to enhance the efficiency and/or effectiveness of the surgical procedure.

As additional points for coarse registration, other well-known points or areas can also be used instead or in addition to the above such as pubic symphysis.

Registration Approaches without Pre-Operative CT

Intra-Operative Fluoroscopy Registration

In certain implementations, registration approaches can be performed without necessarily requiring a pre-operative CT, e.g., CT images 5100 (FIG. 16). It should be noted that certain of these approaches can benefit from additional data gathered from CT images 5100, which can be obtained according to various implementations described herein (e.g., with respect to FIGS. 12-19).

Figure 20:
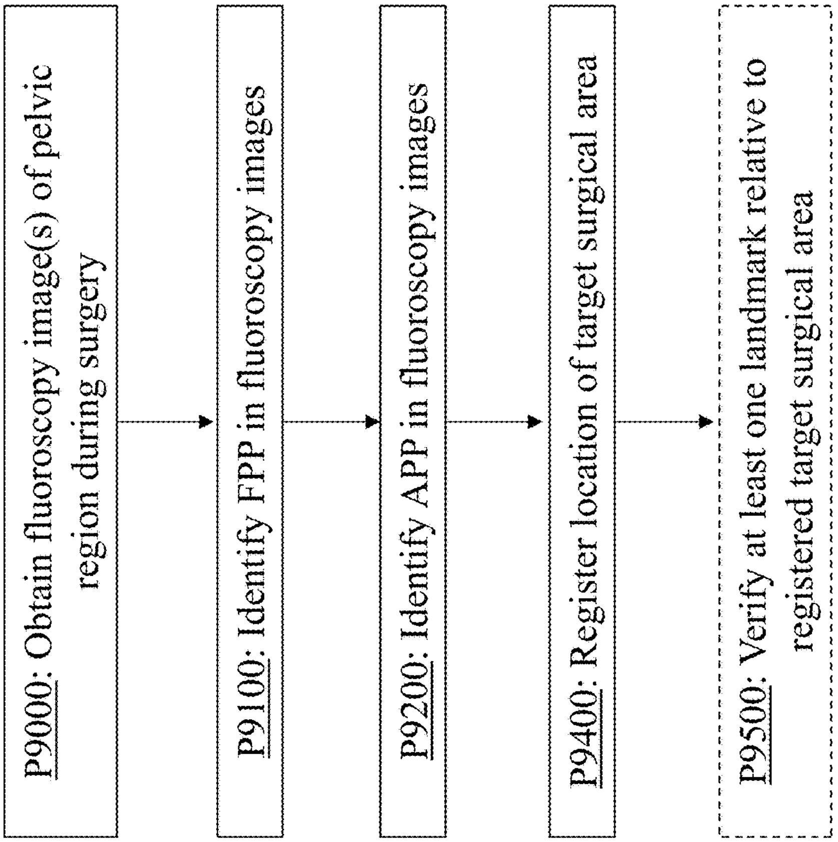
FIG. 20 illustrates a flowchart for registration of a target surgical area of a patient, in accordance with further embodiments of the present disclosure.

FIG. 20 is a flow diagram including registration processes according to various additional implementations. In certain cases, processes performed with reference to FIG. 20 can be executed or otherwise managed by any computer platform herein, e.g., computer platform 400 shown and described with reference to FIG. 16. In certain cases, processes illustrated with reference to FIG. 20 can be performed without necessarily using CT images 5100 and/or first or second ANN(s) 5400, 5500. It is understood, however, that one or more ANNs can be used in conjunction with processes in FIG. 20. Further, verification of registration processes described with reference to FIG. 20 can be performed using CT images 5100, where available and/or desirable.

In any case, turning to FIG. 20, processes in registering a patient as performed by registration module 5000 can include:

in process P9000, obtaining a plurality of fluoroscopy images 5200 at different angles or orientation of the pelvic region of the patient captured during the surgery. In these processes, the fluoroscopy images 5200 are captured while the patient is in the surgical space, e.g., on the surgical table. Processes for obtaining fluoroscopy images 5200 are described and illustrated relative to FIGS. 12-15, e.g., in process P4100. As noted herein, in particular cases, the fluoroscopy images of the pelvic region can include both target and non-target surgical areas in some cases. In particular, the fluoroscopy images 5200 can include orthogonal images such as anterior/posterior (AP) images (or, "shots") of the pelvic region, and lateral images (or, shots) of the pelvic region, or two oblique angle fluoro shots.

In one embodiment, an additional image processing may be helpful, especially on the lateral fluoroscopy image not only due to the presence of a femur, but the image contains femurs of both legs and acetabulum of both legs. The ANN can be used to remove the acetabulum and femur of the side that is not being operated on.

As described below, the registration process can use either the FPP or the APP or both.

Process P9100 includes identifying the functional pelvic plane (FPP) in the fluoroscopy images 5200. The FPP plane is defined as the 2D AP image/shot plane passing through the acetabulum Center of Rotation. This plane is parallel to the table when the patient is in supine position, or orthogonal to the table when the patient is in lateral position.

In particular cases, identifying the FPP is done by identifying a center of rotation of the acetabulum on both the lateral image of the pelvic region and the AP image of the pelvic region. In some cases, the FPP is identified using the center of rotation of the acetabulum, as discussed previously herein.

Figure 21:
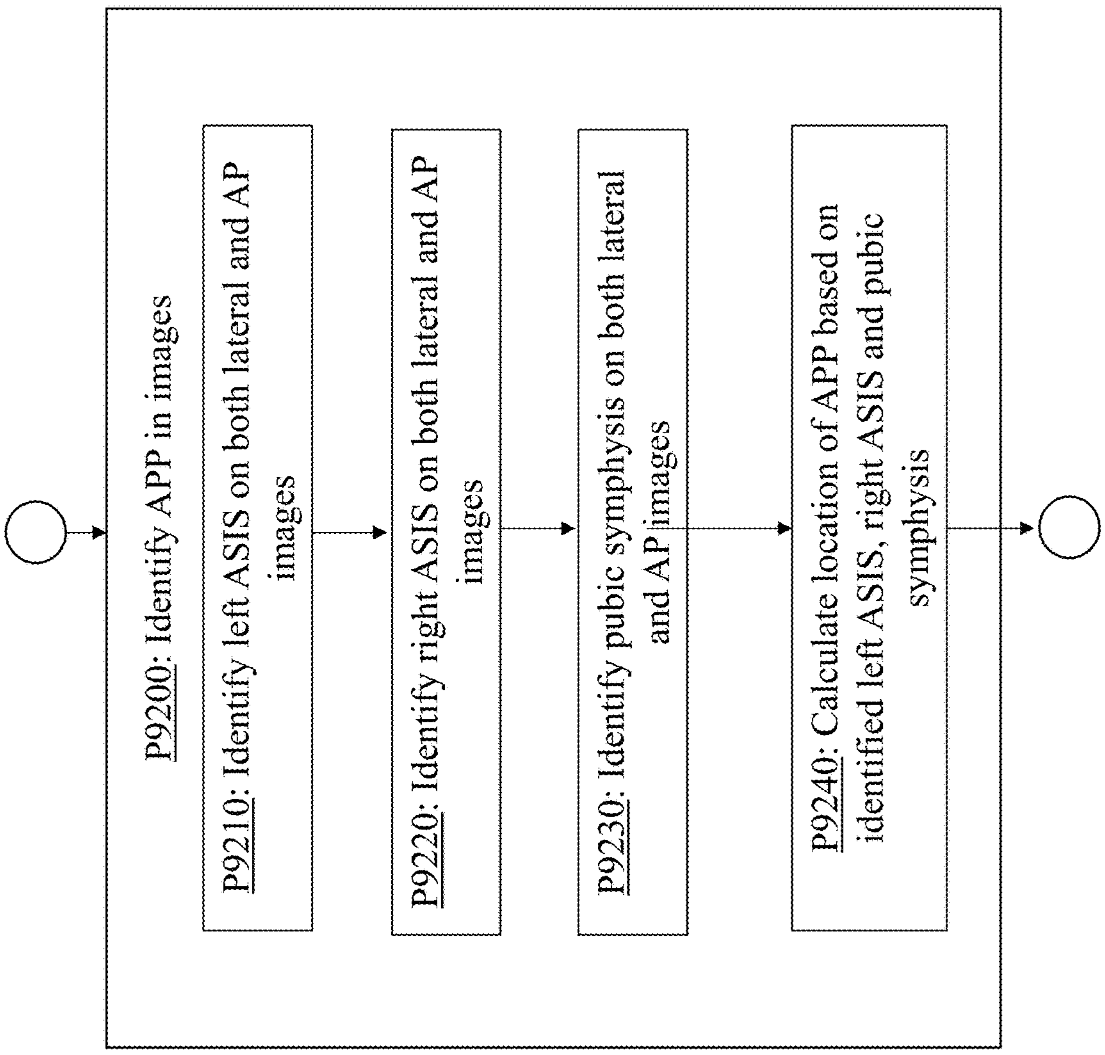
FIG. 21 illustrates sub-processes in the flowchart of FIG. 20, in accordance with some embodiments of the present disclosure.

Process P9200 includes identifying the anterior pelvic plane (APP) in the images 5200. In some cases, identifying the APP is performed after identifying the FPP, however, in other cases, the order can be reversed. In a particular example, identifying (either automatically by the registration software 5000 or semi-automatically or manually by the user) the APP can include various sub-processes, illustrated in the flow diagram in FIG. 21 as:

- process P9210, including identifying a left anterior superior iliac spine (ASIS) on both the lateral image 5200 and the AP image 5200,
- process P9220, including identifying a right ASIS on both the lateral image 5200 and the AP image 5200,
- process P9230, including identifying a pubic symphysis on both the lateral image 5200 and the AP image 5200, and
- process P9240, including calculating a location of the APP based on the identified left ASIS, right ASIS, and pubic symphysis.

Once either the FPP and APP are derived, alignment of the fluoro images to the patient is basically complete.

The registration module 5000 is further configured in process P9400 to register the location of the target surgical area based on either the FPP and APP or both. Registration can be performed according to any approach herein, e.g., producing a registration matrix 5700 and/or model 5800 (FIG. 16), which can be used to enhance the surgical procedure, e.g., THA surgery.

In particular optional implementations, a post-registration process shown in FIG. 20 can include process P9500, which includes verifying at least one landmark (e.g., one or more distal and/or posterior points from a point cloud) relative to the registered target surgical area. Landmark detection is described herein relative to various navigated instrument embodiments and can utilize points in a point cloud. For example, the registration module 5000 can be configured to use inputs from a navigated instrument (e.g., stylus 500, FIG. 5) to verify at least one landmark (such as a pubic symphysis, a divot point on the DRB 6200 or the same on a surveillance marker attached to the pelvis) relative to the registered location of the target surgical area. The registration module 5000 can be configured to verify the registered patient in response to the landmark(s) aligning with locations in the registration matrix 5700 and/or model 5800.

Further optional implementations can include additional post-registration action(s), such as using inputs from a navigated instrument (e.g., stylus 500, FIG. 5) and/or an additional pelvic patient tracker (e.g., patient tracker 6200, FIG. 14) to determine a location of an incision relative to the target surgical area. In certain of these cases, the input from the navigated instrument (e.g., stylus 500, FIG. 5) can indicate a location of a verification divot on the patient. In some examples, the verification divot enables confirmation of navigational integrity during movement of the navigated instrument (e.g., stylus 500, FIG. 5) relative to the surgical area.

In addition to the above-noted processes in identifying the APP and FPP, the registration module 5000 can be further configured (e.g., programmed) to verify or otherwise determine an orientation of the APP and/or the FPP of the patient based on the identified set of locations at which the navigated instrument (e.g., stylus 500, FIG. 5) is palpating the landmark and based on the determined center of rotation for the pelvic acetabulum. In some embodiments, to determine the orientation of the APP, the landmark is defined as the right ASIS, left ASIS, and/or pubic symphysis of the pelvic bone of the patient. Alternatively, in some embodiments, to determine the orientation of the APP based on the identified set of locations at which the navigated instrument is palpating the landmark, the registration module 5000 is further operative to identify an inferior-superior axis, a left-right axis, and/or an antero-posterior axis of the pelvic bone of the patient. In some embodiments, to determine the orientation of the FPP based on the identified set of locations at which the navigated instrument is palpating the landmark, the registration module 5000 is further operative to identify an inferior-superior axis, a left-right axis, and/or an antero-posterior axis of the pelvic bone of the patient. For example, the identification of the inferior-superior axis, the left-right axis, and/or the antero-posterior axis of the pelvic bone of the patient may be performed. In some embodiments, when determining the center of rotation for the pelvic acetabulum, the landmark is defined as the deepest point of the acetabular fossa of the pelvic bone.

In any case, the above-noted processes can enable effective and efficient registration and/or verification of a patient without necessarily requiring pre-operative CT imaging.

Intra-Operative Fluoroscopy with Navigated Instrument Registration

As noted herein, certain aspects of intra-operative fluoroscopy can pose challenges when trying to identify a target surgical area for a patient. In a particular example, it can be difficult to capture a sufficiently precise lateral image of a patient in a surgical area, with significant variation being attributable to the skill of the fluoroscopy machine operator, patient anatomy, as well as other factors. In various additional implementations, the lateral imaging (or, lateral shot) can be supplemented or replaced in an approach similar to those described with reference to FIGS. 20 and 21. In a particular implementation, a single intra-operative 2D fluoroscopy image of a patient can be used to register the target surgical area, with the aid of a navigated instrument and/or femur tracker.

In particular, in certain additional implementations, a center of rotation (CoR) of the target surgical area (e.g., acetabulum) can be determined using one or more supplemental location approaches.

Figure 22:
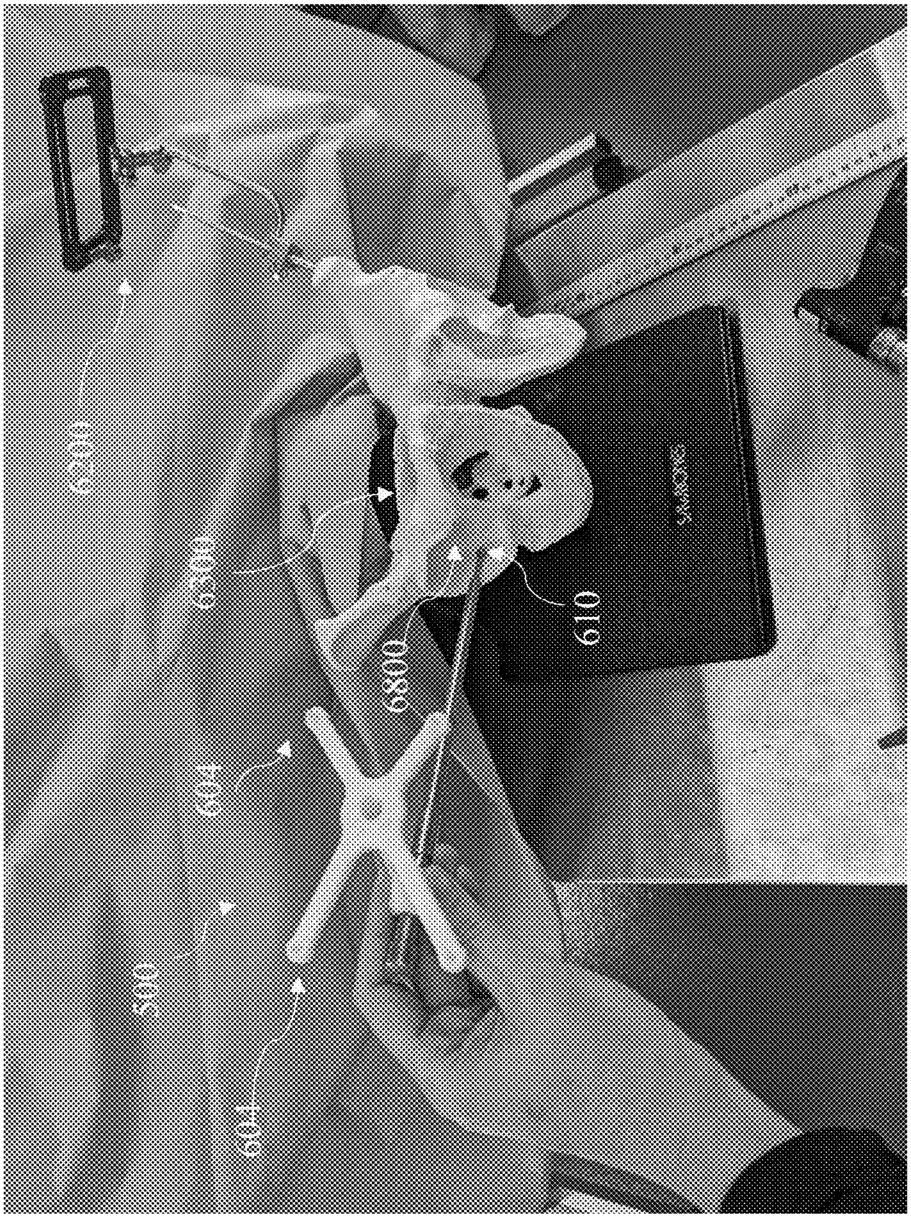
FIG. 22 illustrates a navigated instrument used in obtaining point cloud data from a target surgical area, in accordance with some embodiments of the present disclosure.

In one example, as depicted in the schematic view of a patient model 6300 in FIG. 22, a navigated instrument (e.g., stylus) 500 is depicted as used to trace (or, "paint") a target surgical area (e.g., acetabulum) 6800 to aid in verification of fluoroscopy imaging and/or registration of the target area 6800. FIG. 22 is referred to in conjunction with FIGS. 12-16.

Figure 23:
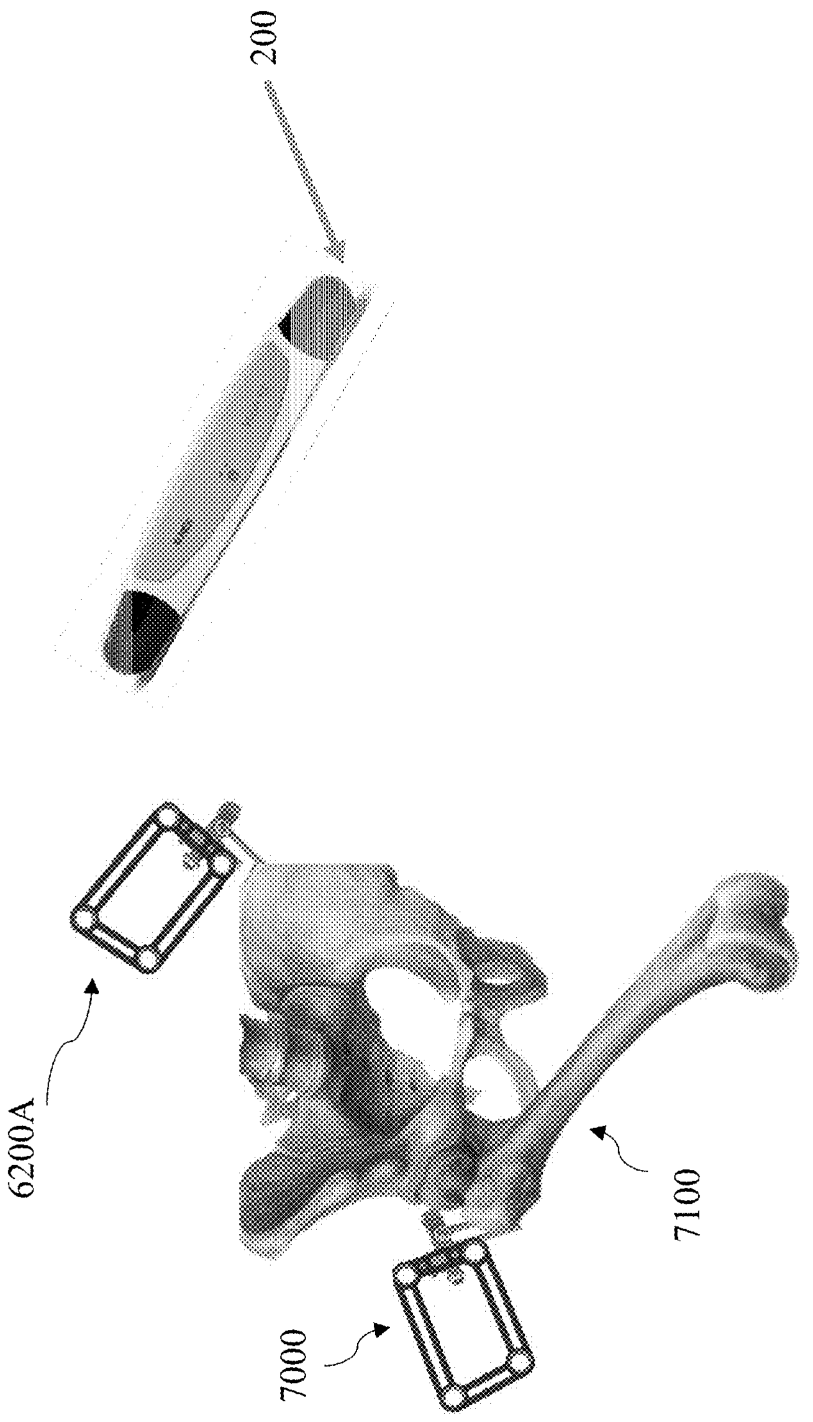
FIG. 23 shows a schematic view of a system for registering a patient according to various additional implementations.

In additional examples, a femur tracker 7000 (FIG. 23) is attached to the patient femur to aid in tracking movement of the patient's femur relative to the target surgical area (e.g., acetabulum). The femur tracker 7000 can be used in conjunction with additional patient trackers as described herein. In FIG. 23, one patient tracker 6200 attached to the pelvis is shown although two or more pelvis trackers can be used. In addition to the femur tracker 7000, certain approaches can benefit from use of a navigation camera 200 (e.g., similar to any navigation camera and/or optical system described herein).

Figure 24:
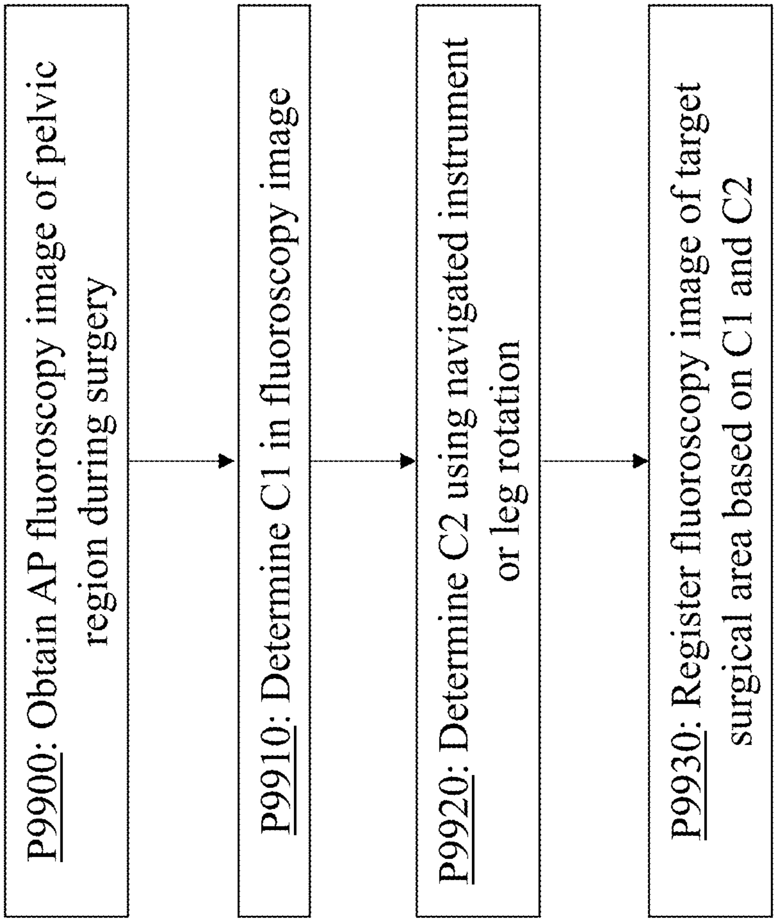
FIG. 24 illustrates a flowchart for registration of a target surgical area of a patient, in accordance with additional embodiments of the present disclosure.

FIG. 24 is a flow diagram illustrating processes in a method of registering a patient according to various implementations, e.g., using registration module 5000 (FIG. 16). These approaches can include registering the patient based on a determined CoR of the acetabulum from at least two distinct methodologies. In particular cases, one methodology can include using a navigated instrument (e.g., as illustrated in FIG. 22) and/or a femur tracker (e.g., as illustrated in FIG. 23). In some cases, the process can include the following.

Process P9900, including obtaining a fluoroscopy image 5200 of the pelvic region of the patient captured during the surgery. As noted herein, in some cases, the fluoroscopy images 5200 of the pelvic region can include a target surgical area 6800 (e.g., acetabulum in FIG. 22) and a non-target surgical area (e.g., portion(s) of the femur or other bones). In some cases, this process can be performed in a substantially similar manner as process P9000 (FIG. 20). In particular implementations, a single fluoroscopy image 5200, such as an AP fluoroscopy image (or AP shot) can be used in the registration process.

Figure 25:
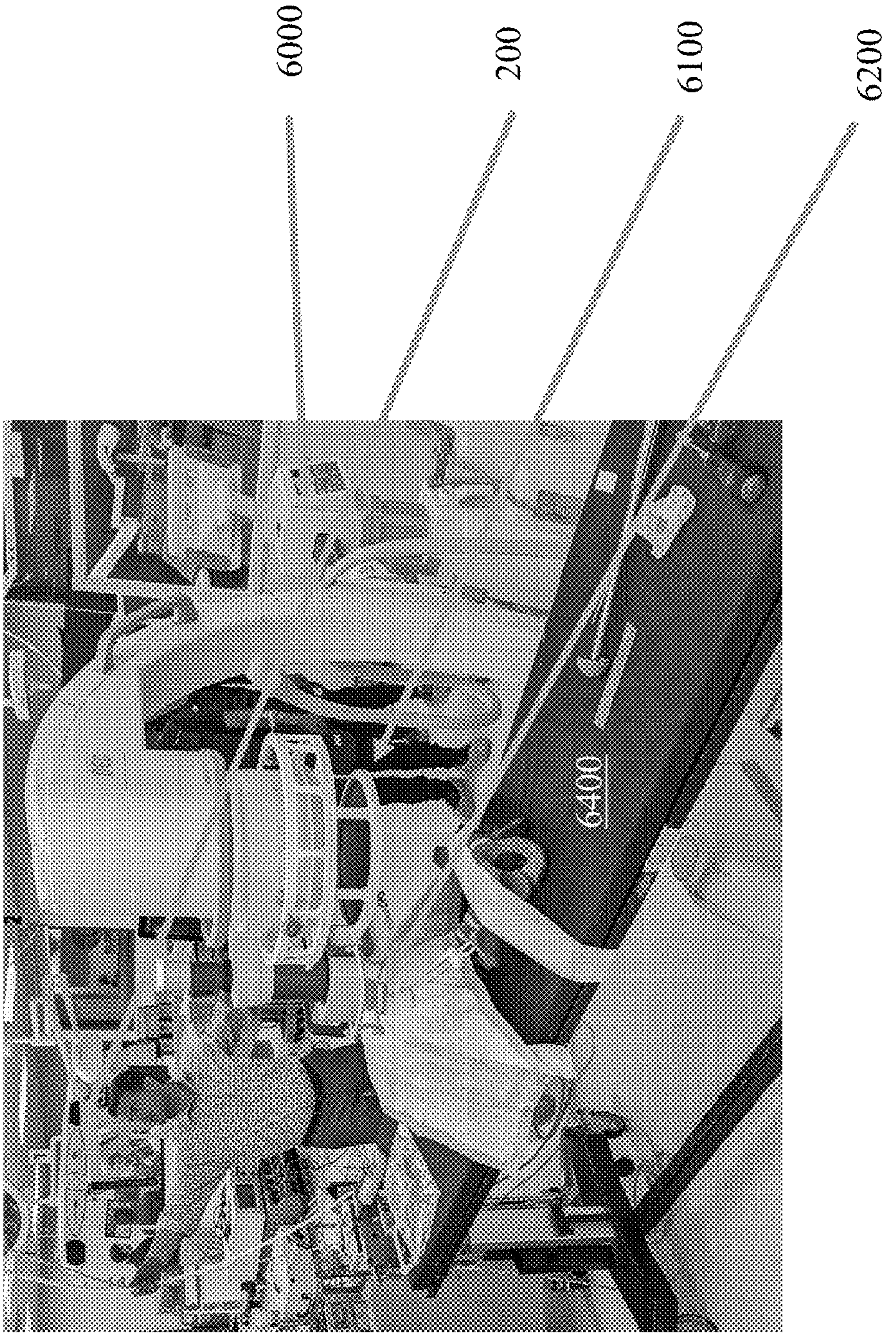
FIG. 25 illustrates an operating room according to some example configurations and systems of the present disclosure.

In a particular implementation, a surgical space (or, operating room) 8000 such as shown in FIG. 25 can be configured such that a fluoroscopy machine 6000 such as a C-arm fluoroscopy machine is positioned over the operating table 6400. A fluoroscopy fixture 6100 is positioned to capture an AP image of the patient on the table, e.g., including location(s) of the patient tracker(s) 6200. In certain cases, the fixture 6100 contains two sets of radiopaque markers on different planes, as well as a set of optical markers trackable by the camera(s). A camera tracking system 200 can also be used as described herein. Various of these features are described with respect to FIG. 14 and are not repeated herein. In this approach, the fluoroscopy fixture 6100 is placed overhead relative to the patient on the operating table 6400, and in particular cases, the AP image is obtained at approximately 90 degrees relative to the patient such that the image accurately captures (or defines) the functional pelvic plane (FPP). Following setup, an AP image of the patient can be obtained while the camera 200 is recording the position of the fixture 6100 and the pelvis patient tracker 6200. While lateral shots can be obtained in some cases, in some additional implementations, lateral shots are either not obtained as part of process P9900 or are otherwise ignored or discounted in the registration processes herein.

Figure 26:
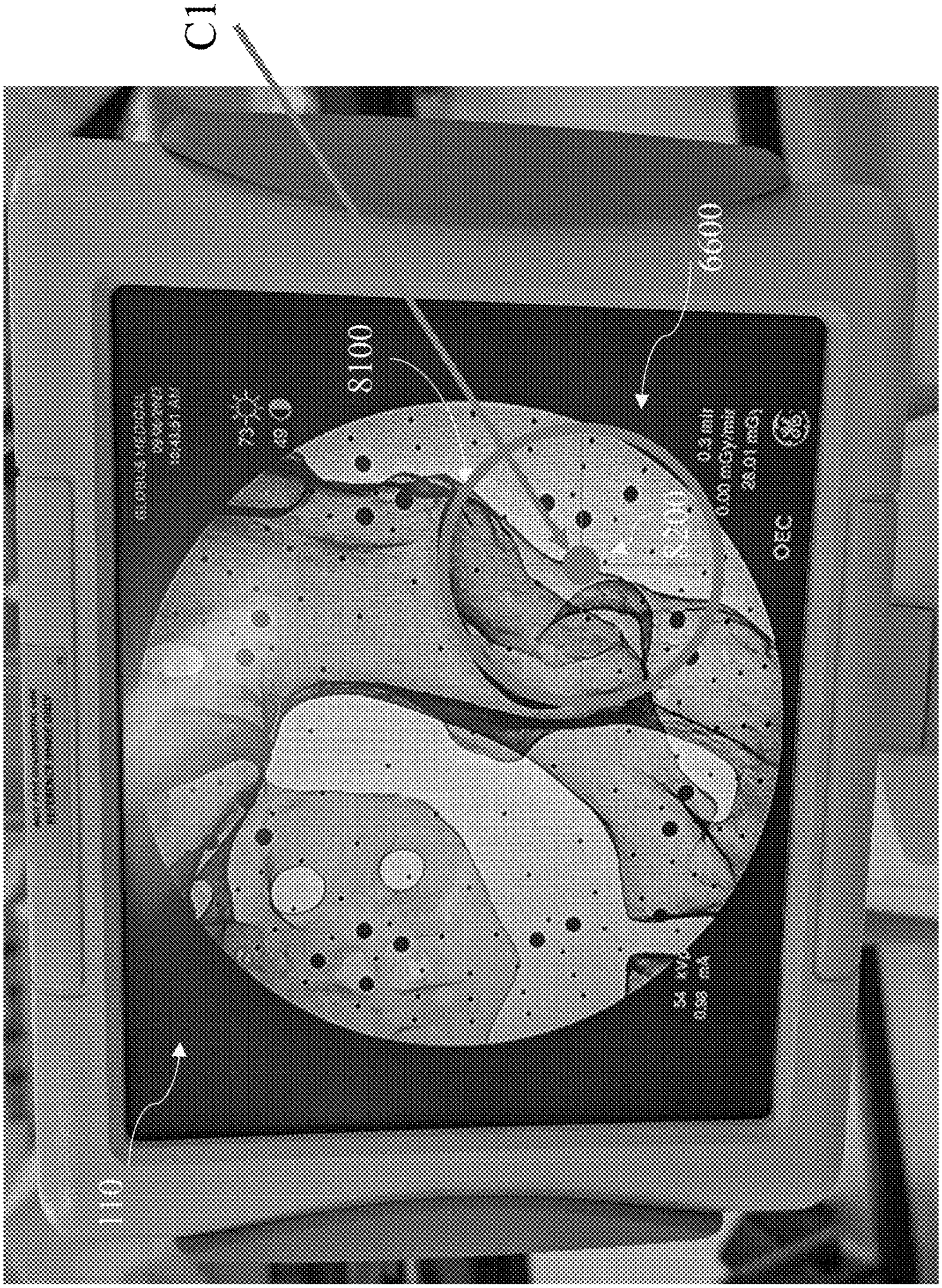
FIGS. 26-29 illustrate approaches in identifying a center of rotation of an acetabulum according to various additional implementations herein.

Process P9910 includes determining a first center of rotation (C1) of the target surgical area (e.g., acetabulum) in the fluoroscopy image 6600 (FIG. 26). In some of these cases, determining C1 includes receiving user input about a curvature of the acetabulum, e.g., as identified on the image 6600. In some examples, the user can review the image 600 on a display 110 and identify the curvature of the acetabulum. The computer platform may be operative to generate C1 based on the identified curvature of the acetabulum. In particular cases, the computer platform is operative to generate a boundary 8100 and a center point 8200 of the boundary as C1. In particular cases, as C1 is identified on a two-dimensional image, C1 is a two-dimensional coordinate. Alone, this two-dimensional coordinate may be insufficiently precise for locating the surgical area. As such, in certain cases, an additional process (FIG. 24) includes:

P9920: determine a second center of rotation (C2) of the acetabulum of the patient using a navigated instrument 500 (FIG. 22) trackable by an optical tracking device (e.g., camera 200). In some cases, C2 is established using navigated instrument 500 and localization of biomechanical landmarks, e.g., on patient trackers 6200. As noted herein, this location (C2) is a three-dimensional coordinate.

In particular cases, the navigated instrument 500 is used to obtain point cloud data from the acetabulum, e.g., as described with reference to FIG. 22. In certain cases, as described herein, the navigated instrument 500 is used to paint the acetabulum while camera(s) 200 continuously track and record the position of the navigated instrument 500, e.g., by zigzagging across the concave interior wall of the acetabulum until a sufficient number of points are collected for the computer platform to derive a sphere. In some cases, the computer platform is operative to identify C2 using the point cloud data. For example, C2 can be identified as a center point in a best fit sphere defined by the point cloud data.

Figure 27:
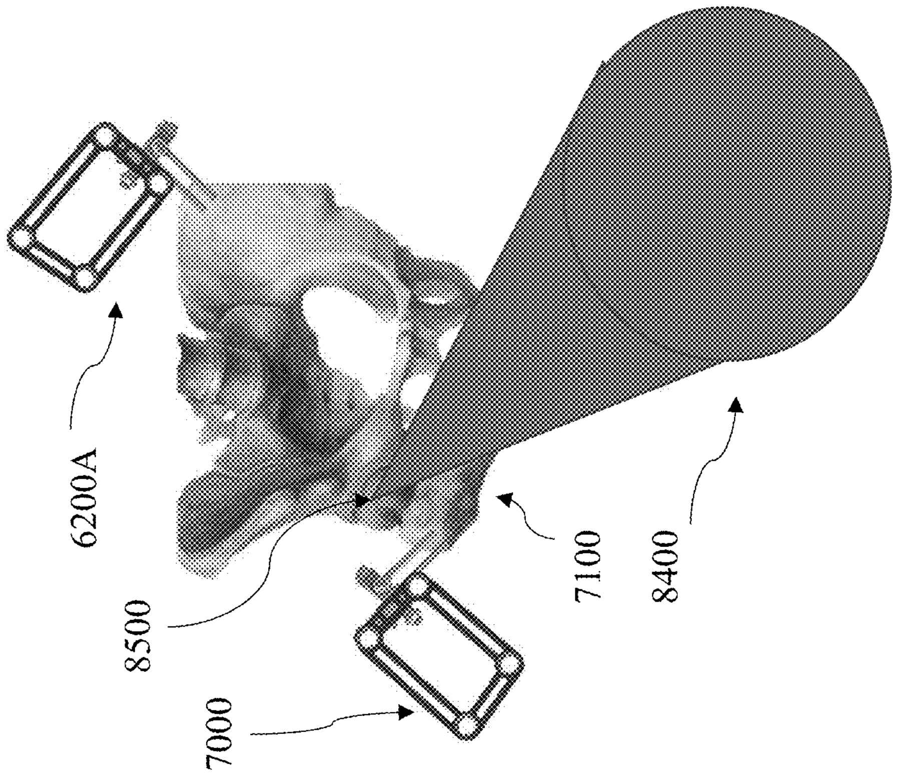
Figure 28:
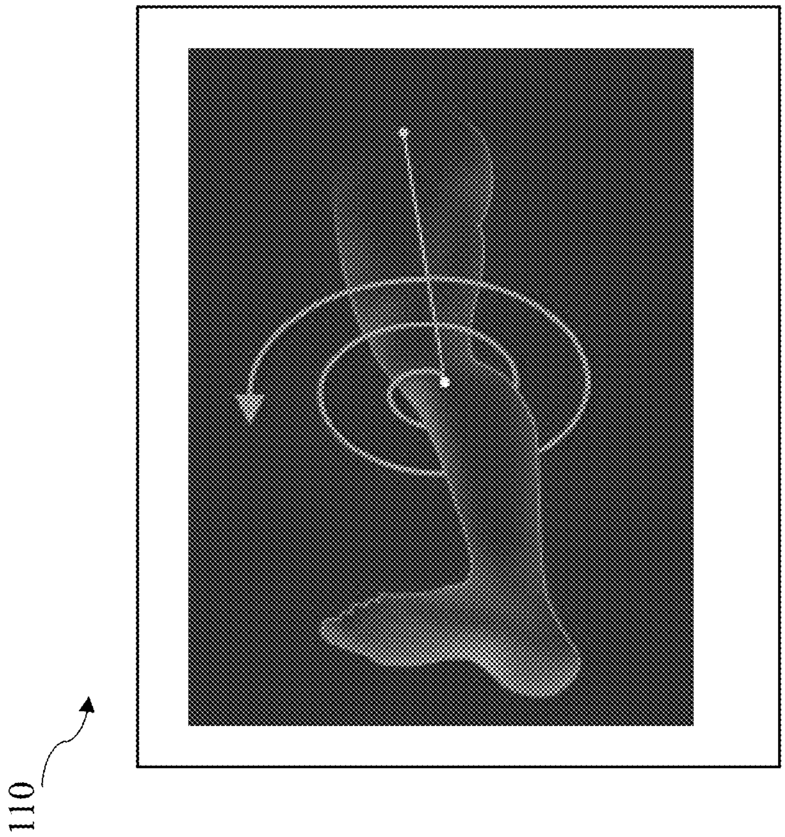

In other particular cases, determining C2 is performed using a femur tracker 7000 (FIG. 23). In these cases, the femur tracker 7000 having a set of tracking markers is attached to the patient, e.g., proximate a base of the femur. In such cases, a further process can include manipulating the patient's leg (to which femur tracker 7000 is attached). For example, FIG. 28 shows a display 110 including visual guidance for an operator to manipulate (e.g., rotate in a circular motion) the patient's leg about the ball/socket joint of the acetabulum. FIG. 27 illustrates how three-dimensional (3D) cone data 8400 representing manipulation of the leg of the patient relative to a center of rotation can be obtained during the manipulation. Because the hip is a ball-and-socket joint, manipulation of the leg allows the camera tracking system to monitor the femur tracker 7000 and generate data representing a cone 8400 that can be referenced to the acetabulum. In other terms, the 3D data 8400 represents a range of motion of the leg of the patient relative to the acetabulum. In particular cases, the center 8500 of the 3D cone data 8400 can be identified as C2. In practice, the points collected represent the surface of a hemisphere whose center is a known point for use as C2.

Returning to FIG. 24, in further implementations, the fluoroscopy image 6600 is registered (process P9930) based on the identified C1 and C2. In certain cases, registering the fluoroscopy image includes mating C1 and C2 coincident using vector manipulation. C1 and C2 are made coincident and mated to a single location in three-dimensional space. Based on the matching, a pelvic plane (FPP) in the fluoroscopy images 5200 is derived. The CoR assists with determining a relative height of the CoR in the AP fluoro image to the actual height of the CoR of the patient, thus completing the alignment process.

Based on the matched CoR and/or derived FPP, registration can be performed according to any approach herein, e.g., producing a registration matrix 5700 and/or model

5800 (FIG. 16), which can be used to enhance the surgical procedure, e.g., THA surgery.

Figure 29:
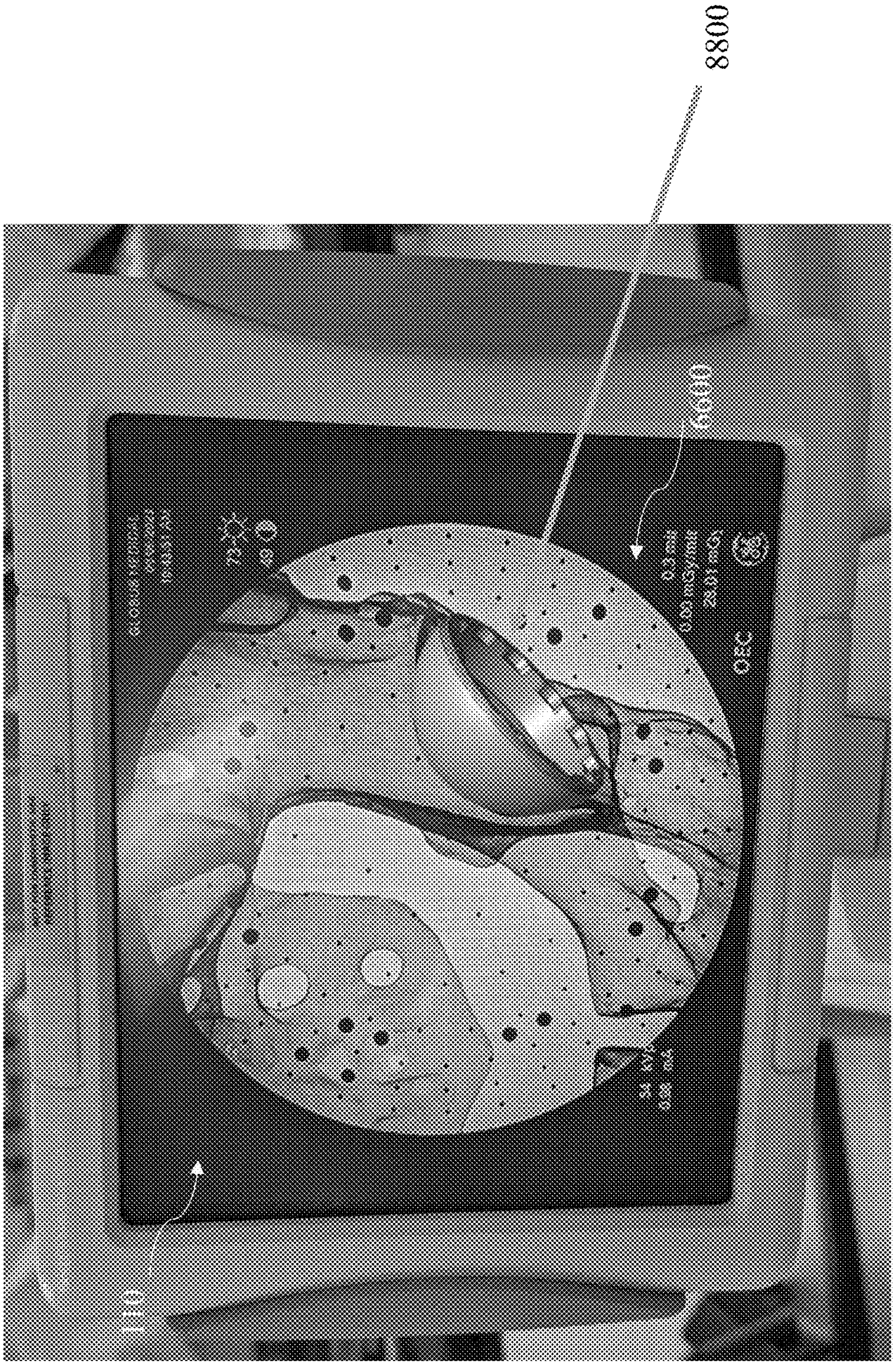

In some optional additional cases, as illustrated in FIG. 29, the location of an implant 8800 can be planned on an image 6600 based on the registered location.

Further optional implementations can include additional post-registration action, such as using inputs from a navigated instrument (e.g., stylus 500, FIG. 5) and/or an additional pelvic patient tracker (e.g., patient tracker 6200, FIGS. 14, 22) to determine a location of an incision relative to the target surgical area. In certain of these cases, the input from the navigated instrument (e.g., stylus 500, FIG. 22) can indicate a location of a verification divot on the patient. In some examples, the verification divot enables confirmation of navigational integrity during movement of the navigated instrument (e.g., stylus 500, FIG. 5) relative to the surgical area.

In all registration workflows described above, after the registration process is completed, the verification step may involve the following steps. The registration software 5000 displays a landmark over an expected location of a displayed bone anatomy containing the targeted area and asks the user to touch the same landmark on the patient with the navigated instrument 500 while the instrument is being tracked by the cameras 200 and being continuously displayed over the displayed anatomy. The user is able to watch the display and verify that the point being touched by the navigated instrument 500 is at the same location of the expected location. The registration software 5000 then may automatically confirm the locations or receive user input confirming the locations at which time the registration is verified.

Additional Assessment Examples

Additional optional implementations can include identifying a functional pelvic plane (FPP) in the plurality of fluoroscopy images 5200. Identifying the FPP can be performed in a similar manner as process P9100 (FIG. 20), and can be based on fluoroscopy images 5200 from one or more angles relative to the patient. In particular implementations, the FPP is identified based on one or more AP images of the pelvic region. In more particular examples, the FPP is identified by excluding or otherwise discounting lateral fluoroscopy images 5200 of the patient.

In certain cases, the FPP is verified using the identified center of rotation of the acetabulum, e.g., from the AP image of the pelvic region. In further cases, identification of the inferior-superior axis, the left-right axis, and/or the antero-posterior axis of the pelvic bone of the patient may be performed. In some embodiments, when determining the center of rotation for the pelvic acetabulum 6800, the landmark is defined as the deepest point of the acetabular fossa of the pelvic bone.

In addition to the above-noted processes in identifying the APP and FPP, the registration module 5000 can be further configured (e.g., programmed) to verify or otherwise determine an orientation of the APP and/or the FPP of the patient based on the identified set of locations at which the navigated instrument (e.g., stylus 500, FIG. 5) is palpating the landmark and based on the determined center of rotation for the pelvic acetabulum. In some embodiments, to determine the orientation of the APP, the landmark is defined as the right ASIS, left ASIS, and/or pubic symphysis of the pelvic bone of the patient. Alternatively, in some embodiments, to determine the orientation of the APP based on the identified set of locations at which the navigated instrument is palpating the landmark, the registration module 5000 is further operative to identify an inferior-superior axis, a left-right axis, and/or an antero-posterior axis of the pelvic bone of the patient. In some embodiments, to determine the orientation of the FPP based on the identified set of locations at which the navigated instrument is palpating the landmark, the registration module 5000 is further operative to identify an inferior-superior axis, a left-right axis, and/or an antero-posterior axis of the pelvic bone of the patient.

In a similar way to the pre-operative patient assessment, a post-operative patient assessment can be executed by the surgeon to assess the quality of the THA surgery and the benefits to the patient. The workflow can include a patient mobility evaluation, e.g., with data collected from physical exercises and sensor feedback (e.g., attached to the leg), and which can be compared to clinical surveys to confirm the patient's health status. All gathered post-operative information can be automatically compared by the system to the pre-operative information.

The bone palpation operations can be used in many ways to acquire and extract landmarks, which may vary based on whether the operations are for a computer assisted navigation procedure (e.g., robotic) versus manual navigated procedure, and whether the operations are used with an imageless or CT-based procedure.

For example, in a patient registration workflow for computer assisted navigation procedure or manual navigated procedure with imageless or CT images-based, the bone palpation operations can be used to acquire and extract landmarks.

In a workflow for display of a bone 3D model for a computer assisted navigation procedure: for an imageless process, a generic bone model can have dimensions updated based on acquired and extracted landmarks through bone palpation operations; or for a CT image-based process, a reconstructed 3D model of the patient anatomy can be generated based on pre-operative CT images and based on acquired and extracted landmarks through bone palpation operations.

In a workflow for display of a bone 3D model for a manual navigated procedure: for an imageless process, a generic bone model may not have dimensions updated based on acquired and extracted landmarks through bone palpation operations; or for a CT image-based process a reconstructed 3D model of the patient anatomy can be generated based on pre-operative CT images and may or may not be based on acquired and extracted landmarks through bone palpation operations.

In a workflow for display of navigated instruments together with a bone model for a computer assisted navigation procedure: for an imageless process, no navigated instrument may be displayed together with the bone 3D model; or for a CT image-based process, a navigated saw blade may be displayed together with the bone 3D model.

In a workflow for display of a bone 3D model for a manual navigated procedure, for an imageless or CT image-based process, a navigation instrument and planned trajectory of various implants or cuts may be displayed together with a bone 3D model to guide the user.

The computer platform may be further operative to determine an orientation of an anterior pelvic plane (APP) and/or a functional pelvic plane (FPP) of the patient based on the identified set of locations at which the navigated instrument is palpating the landmark and based on the determined center of rotation for the pelvic acetabulum.

In some embodiments, to determine the orientation of the APP, the landmark is defined as the right ASIS, left ASIS, and pubic symphysis of the pelvic bone of the patient.

Alternatively, in some embodiments, to determine the orientation of the APP based on the identified set of locations at which the navigated instrument is palpating the landmark, the computer platform is further operative to identify an inferior-superior axis, a left-right axis, and/or an antero-posterior axis of the pelvic bone of the patient.

In some embodiments, to determine the orientation of the FPP based on the identified set of locations at which the navigated instrument is palpating the landmark, the computer platform 400 is further operative to identify an inferior-superior axis, a left-right axis, and/or an antero-posterior axis of the pelvic bone of the patient. For example, the identification of the inferior-superior axis, the left-right axis, and/or the antero-posterior axis of the pelvic bone of the patient may be performed. In some embodiments, when determining the center of rotation for the pelvic acetabulum, the landmark is defined as the deepest point of the acetabular fossa of the pelvic bone.

In some embodiments, the inferior-superior axis is identified by a rod on the navigated instrument being parallel to the inferior superior axis while the navigated instrument is palpating the landmark.

In some embodiments, the computer platform 400 is further operative to identify another location at which the navigated instrument is palpating a deepest point on an acetabular fossa. The computer platform may further be operative to determine a maximum acetabular reaming depth based on the identified another location at which the navigated instrument palpated the deepest point on the acetabular fossa.

In some embodiments, the orientation of the APP and/or the FPP, and the center of rotation for pelvic acetabulum, is determined without the use of pre-operative images.

In some embodiments, the computer platform 400 is further operative to register the determined orientation of the APP and/or the FPP in an algorithm for computer assisted navigation during surgery. Additionally, in some embodiments, the computer platform is further operative to display a graphical representation of the determined orientation of the APP and/or the FPP in a planning view for computer assisted navigation during surgery.

In some embodiments, after determining the orientation of the APP and/or the FPP based on the identified set of locations at which the navigated instrument is palpating the landmark and based on the determined center of rotation for the pelvic acetabulum, the computer platform 400 is further operative to identify a first location, separate from the set of locations, at which the navigated instrument palpates a proximal femoral greater trochanter region at least proximate to an exit point of a femoral anatomical axis. In these embodiments, the computer platform 400 is further operative to identify a second location, separate from the set of locations, at which the navigated instrument palpates a distal part of the femur where an electrocardiogram (EKG) patch electrode is located on the patient. Additionally, in some embodiments, the computer platform 400 is further operative to determine length of a leg of the patient and a medio-lateral femur positioning offset based on the identified first location and identified second location.

Additionally, in these embodiments, the identification of another location, separate from the set of locations, at which the navigated instrument 500 (FIG. 5) palpates the proximal femoral greater trochanter region at least proximate to the exit point of the femoral anatomical axis is performed after a femur of the patient is placed in a known position.

In some embodiments, the navigated instrument comprises a ball tip stylus. For example, the ball tip stylus may correspond to the ball tip stylus 500 of FIG. 5. The computer platform 400 can be operative to identify the set of locations at which the navigated instrument is palpating the landmark by identifying locations of fiducials of a reference element on a ball tip stylus in images being obtained from tracking cameras with at least partially overlapping fields-of-view which image the ball tip stylus with a ball on the ball tip stylus palpating the surface of the bone. Further, the computer platform 400 may be operative to identify the set of locations by determining locations of a center of the ball based on the locations of the fiducials of the reference element; define an offset-acquired surface of the bone based on mathematically connecting the locations of the center of the ball; determine local normal vectors to the offset-acquired surface for the locations of the center of the ball; and translate the offset-acquired surface of the bone toward the surface of the bone along the local normal vectors based on a radius of the ball to define an acquired surface of the bone.

In some embodiments, the computer platform 400 is further operative to determine a center of rotation for a pelvic acetabular of the patient based on the identified set of locations at which the navigated instrument is palpating the landmark comprising an inside of an acetabulum cavity of the patient, and determine the origin of the APP and/or FPP based on the center of rotation for the pelvic acetabular of the patient. In these embodiments, the determination of the center of rotation for the pelvic acetabular of the patient can be performed after a femoral head of a femur of the patient is removed from the acetabular cavity. Additionally or alternatively, the computer platform 400 is further operative to generate a model of the shape of the acetabulum cavity based on the identified set of locations at which the navigated instrument is palpating the landmark comprising the inside of the acetabulum cavity of the patient.

In some embodiments, the computer platform 400 is further operative to register in an algorithm for computer assisted navigation during surgery, at least one of the determined orientation of the APP, determined orientation of the FPP, and determined center of rotation for the pelvic acetabulum. In some embodiments, the orientation of the APP and/or the FPP of the patient is determined further based on a gravity vector of an inbuilt inertial measurement unit (IMU) of a tracking camera of the system.

As described above and in summary, various embodiments enable patient registration for a surgery such as a THA surgery. THA surgery may present particular registration-related challenges, for example, where anatomical features make imaging more challenging and/or where surgical access to such features is limited. As noted herein, imaging of the pelvic operating area (or, acetabulum) often includes non-target regions such as the femur, and imaging of that operating area can present challenges in effective (e.g., precise) patient registration. The various disclosed embodiments enable precise patient registration using one or more imaging techniques. These disclosed embodiments can provide additional, effective options for patient registration that are adaptable based on one or more factors, e.g., availability and/or quality of imaging, patient anatomy, skill and/or availability of technicians, etc. In any case, the disclosed embodiments have the technical effect of enhancing surgical patient registration, e.g., for a procedure such as THA surgery.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being “connected”, “coupled”, “responsive”, or variants thereof to another element, it can be directly connected, coupled, or responsive to the other element or intervening elements may be present. In contrast, when an element is referred to as being “directly connected”, “directly coupled”, “directly responsive”, or variants thereof to another element, there are no intervening elements present. Like numbers refer to like elements throughout. Furthermore, “coupled”, “connected”, “responsive”, or variants thereof as used herein may include wirelessly coupled, connected, or responsive. As used herein, the singular forms “a”, “an” and “the” are intended to include the plural forms as well, unless the context clearly indicates otherwise. Well-known functions or constructions may not be described in detail for brevity and/or clarity. The term “and/or” includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms “comprise”, “comprising”, “comprises”, “include”, “including”, “includes”, “have”, “has”, “having”, or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation “e.g.”, which derives from the Latin phrase “exempli gratia,” may be used to introduce or specify a general example or examples of a previously mentioned item, and is not intended to be limiting of such item. The common abbreviation “i.e.”, which derives from the Latin phrase “id est,” may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as “circuitry,” “a module” or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

We claim:

1. A system for computer assisted navigation during a surgery, comprising a computer platform operative to:

obtain a computed tomography (CT) image of a pelvic region of a patient captured prior to the surgery, wherein the CT image of the pelvic region includes a target surgical area and a non-target surgical area, generate from the CT image a three-dimensional (3D) CT volume of the target surgical area which excludes the non-target surgical area;

obtain a fluoroscopy image of the pelvic region of the patient captured during the surgery, merge the 3D CT volume with the fluoroscopy image, and register the target surgical area based on the merged 3D CT volume and fluoroscopy image.

2. The system of claim 1, wherein the surgery includes a total hip arthroplasty.

3. The system of claim 1, wherein the target surgical area includes the acetabulum.

4. The system of claim 1, wherein the fluoroscopy image includes a plurality of fluoroscopy images of the pelvic region that are orthogonal to each other.

5. The system of claim 1, wherein the fluoroscopy image includes the non-target surgical area.

6. The system of claim 1, wherein the non-target surgical area includes at least a portion of a femur of the patient.

7. The system of claim 1, wherein the CT image contain an image of the patient in a supine position.

8. The system of claim 1, wherein applying the set of image merge rules includes applying at least one rule identifying obstructing anatomy in the CT image.

9. The system of claim 1, wherein the merge operation includes:

segmenting the CT image using a first artificial neural network (ANN) to identify a volume of a plurality of bones in the CT image, and generating a 3D bone model for the pelvis which excludes the femur.

10. The system of claim 9, wherein the fluoroscopy image includes at least two fluoroscopy images of the pelvic region.

11. The system of claim 10, wherein the merge operation further includes:

merging the 3D bone model with the at least two fluoroscopy images of the pelvic region using a second artificial neural network (ANN).

12. The system of claim 11, wherein merging the 3D bone model includes:

generating synthetic fluoroscopy images at various projected angles as digitally reconstructed radiographs (DRRs) and comparing the DRRs to the at least two fluoroscopy images, identifying a best match between the DRRs and the fluoroscopy images, and registering the location of the target surgical area based on the best match.

13. The system of claim 11, wherein the first ANN includes a trained machine learning algorithm that is trained by providing a CT image dataset including annotated target surgical areas and non-target surgical areas.

14. The system of claim 11, wherein the second ANN includes a trained machine learning algorithm that is trained by providing a fluoroscopy image data set including annotated target surgical areas and non-target surgical areas.

15. The system of claim 1, wherein registering the target surgical area includes generating a registration matrix of the target surgical area.

16. The system of claim 15, wherein the computer platform further displays the registration matrix on a user interface in a surgical area during the surgery.

17. The system of claim 1, wherein the computer platform is further operative to:

generate a model of the target surgical area based on the registered location.

18. A computer program product comprising a non-transitory computer readable medium storing instructions executable by at least one processor to perform operations for computer assisted navigation during surgery to:

obtain a computed tomography (CT) image of a pelvic region of a patient captured prior to the surgery, wherein the CT image of the pelvic region includes a target surgical area and a non-target surgical area, generate from the CT image a three-dimensional (3D) CT volume of the target surgical area which excludes the non-target surgical area;

obtain a fluoroscopy image of the pelvic region of the patient captured during the surgery, merge the 3D CT volume and the fluoroscopy image, and register the target surgical area based on the merged 3D CT volume and fluoroscopy image.

19. The computer program product of claim 18, wherein the merge includes:

segmenting the CT image using a first artificial neural network (ANN) to identify a volume of a bone in the CT image, and generating the 3D volume for the identified volume, wherein the fluoroscopy image includes at least two fluoroscopy images of the pelvic region.

20. The computer program product of claim 19, wherein the target surgical area includes the acetabulum, wherein the fluoroscopy image includes a plurality of fluoroscopy images of the pelvic region of the patient captured during the surgery and including the non-target surgical area, wherein the non-target surgical area includes at least a portion of a femur of the patient, and wherein the CT image contain an image of the patient in a supine position.

* * * * *